US012048674B2

(12) United States Patent
Yang

(10) Patent No.: US 12,048,674 B2
(45) Date of Patent: Jul. 30, 2024

(54) FULL-AUTOMATIC MEDICATION DISPENSING SYSTEM AND METHOD OF SOLID MEDICATION SEPARATION

(71) Applicant: JB MEDICAL, INC., Ningbo (CN)

(72) Inventor: Jibin Yang, Sparta, NJ (US)

(73) Assignee: JB MEDICAL, INC., Ningbo (CN)

( * ) Notice: Subject to any disclaimer, the term of this patent is extended or adjusted under 35 U.S.C. 154(b) by 304 days.

(21) Appl. No.: 15/756,036

(22) PCT Filed: Aug. 23, 2016

(86) PCT No.: PCT/CN2016/096308
§ 371 (c)(1),
(2) Date: Feb. 27, 2018

(87) PCT Pub. No.: WO2017/032294
PCT Pub. Date: Mar. 2, 2017

(65) Prior Publication Data
US 2018/0263853 A1    Sep. 20, 2018

(30) Foreign Application Priority Data

Aug. 27, 2015 (CN) .......................... 201510532075.9

(51) Int. Cl.
*A61J 7/00* (2006.01)
*A61J 7/02* (2006.01)
(Continued)

(52) U.S. Cl.
CPC ........... *A61J 7/0076* (2013.01); *A61J 7/0084* (2013.01); *A61J 7/02* (2013.01); *A61J 7/0427* (2015.05);
(Continued)

(58) Field of Classification Search
CPC ......... A61J 7/0076; A61J 7/0481; B65B 1/04; B65B 5/103; B65B 35/14; B65B 35/26;
(Continued)

(56) References Cited

U.S. PATENT DOCUMENTS 2,523,517 A * 9/1950 Potter ..................... G06M 7/00
235/132 E
2,744,612 A * 5/1956 Kay ................... B65G 47/1457
198/392
(Continued)

FOREIGN PATENT DOCUMENTS

CN        201745807 U     2/2011
CN        104245515 A    12/2014
(Continued)

OTHER PUBLICATIONS

Chinese Decision of Rejection and Search Report, dated Aug. 21, 2018, for Chinese Application No. 201510532075.9, with English translations.
(Continued)

*Primary Examiner* — Gene O Crawford
*Assistant Examiner* — Kelvin L Randall, Jr.
(74) *Attorney, Agent, or Firm* — Birch, Stewart, Kolasch & Birch, LLP

(57) ABSTRACT

The present invention disclosed a full automatic medication dispensing system and methods of solid medication separation, comprising of a medication feeding device, a medication separation device, a medication distributing channel device, a medication supply device, a medication returning device and a central processing unit. The system has no requirement on the size, shape and weight of solid medications, the medications can be automatically and accurately dispensed into the sealed medication supply box according to the set parameters, and the excessive medications are
(Continued)

automatically returned to the medication retrieving bottles. The system can remind a medication taking person to take the medication in time and supply the medications when confirmed. User can choose a portable medication box or a fixed medication box with a larger capacity. The system can be directly set, and parameters can also be set more conveniently through the mobile client and the reminding functions and the remote setting functions can be added. Medications can be taken in advance. The system can inform preset people when a dose of medications are not taken after a preset period of time, or more medications and medication dispensing are needed, The system can accurately dispense medications, and is convenient to clean, easy to use, and is of great economic, practical and medical value.

18 Claims, 15 Drawing Sheets

(51) Int. Cl.

| | | |
|---|---|---|
| A61J 7/04 | (2006.01) | |
| B65B 1/04 | (2006.01) | |
| B65B 5/10 | (2006.01) | |
| B65B 35/06 | (2006.01) | |
| B65B 35/14 | (2006.01) | |
| B65B 35/26 | (2006.01) | |
| B65B 57/18 | (2006.01) | |
| B65B 57/20 | (2006.01) | |
| B65G 47/14 | (2006.01) | |
| B65G 47/31 | (2006.01) | |
| G16H 20/13 | (2018.01) | |
| B65B 59/04 | (2006.01) | |

(52) U.S. Cl.
CPC ............ *A61J 7/0454* (2015.05); *A61J 7/0481* (2013.01); *B65B 1/04* (2013.01); *B65B 5/103* (2013.01); *B65B 35/06* (2013.01); *B65B 35/14* (2013.01); *B65B 35/26* (2013.01); *B65B 57/18* (2013.01); *B65B 57/20* (2013.01); *B65G 47/1464* (2013.01); *B65G 47/31* (2013.01); *G16H 20/13* (2018.01); *B65B 59/04* (2013.01)

(58) Field of Classification Search
CPC ......... B65B 57/18; B65B 57/20; B65B 59/04; B65G 47/31; B65G 47/1464; G07F 11/24; G07F 11/58; G07F 11/62; G07F 17/0092; G16H 20/13
See application file for complete search history.

(56) References Cited

U.S. PATENT DOCUMENTS

| | | | | | |
|---|---|---|---|---|---|
| 2,865,532 | A * | 12/1958 | Smith | .................... | G07F 11/36 221/13 |
| 2,928,521 | A * | 3/1960 | Johnson | ............... | B65G 47/684 198/392 |
| 3,837,139 | A * | 9/1974 | Roseberg | .................. | A61J 7/02 53/501 |
| 3,986,636 | A * | 10/1976 | Hoppmann | ............. | B65B 5/101 221/7 |
| 4,570,655 | A * | 2/1986 | Raterman | ................ | G07D 9/04 453/10 |
| 4,828,100 | A * | 5/1989 | Hoppmann | ........ | B65G 47/1428 198/392 |
| 4,938,082 | A * | 7/1990 | Buckley | .................... | B07C 5/02 198/392 |
| 4,979,607 | A * | 12/1990 | Fogg | .................. | B65G 47/1457 198/392 |
| 5,369,940 | A * | 12/1994 | Soloman | .................. | B65B 37/12 53/500 |
| 5,638,417 | A * | 6/1997 | Boyer | ........................ | A61J 7/02 377/6 |
| 5,671,262 | A * | 9/1997 | Boyer | ................... | G06M 1/101 377/11 |
| 5,713,454 | A * | 2/1998 | Jordan | .................. | B23P 19/001 198/391 |
| 5,752,368 | A * | 5/1998 | Tobe | ........................ | B65B 5/103 221/3 |
| 5,884,806 | A * | 3/1999 | Boyer | ........................ | A61J 7/02 221/13 |
| 6,377,648 | B1 * | 4/2002 | Culbert | ..................... | A61J 7/02 377/6 |
| 6,401,429 | B2 * | 6/2002 | Aylward | ................. | B65B 5/103 53/244 |
| 6,449,921 | B1 * | 9/2002 | Kim | ......................... | B65B 5/103 53/154 |
| 6,481,180 | B1 * | 11/2002 | Takahashi | ............... | B65B 5/103 221/133 |
| 7,516,836 | B2 * | 4/2009 | Trygar | .................... | B65B 5/103 198/392 |
| 7,669,707 | B2 * | 3/2010 | Kenneway | ................ | B07C 5/02 198/392 |
| 7,861,846 | B1 * | 1/2011 | Salditch | ............. | B65G 47/1457 198/392 |
| 8,078,329 | B2 * | 12/2011 | Boeckx | ................... | B30B 15/32 700/283 |
| 8,360,270 | B1 * | 1/2013 | McClosky | ............... | G07F 11/44 221/2 |
| 8,943,780 | B1 * | 2/2015 | McGonagle | ............ | A61J 1/035 53/396 |
| 9,283,149 | B2 * | 3/2016 | Czarnek | .................... | A61J 7/02 |
| 9,481,482 | B2 * | 11/2016 | Brug | ........................ | B65B 55/00 |
| 2001/0045081 | A1 * | 11/2001 | Aylward | ................. | B65B 5/103 53/244 |
| 2002/0179619 | A1 * | 12/2002 | Geltser | ..................... | A61J 7/02 221/2 |
| 2002/0179623 | A1 * | 12/2002 | Geltser | ............... | G07F 17/0092 221/13 |
| 2003/0111484 | A1 * | 6/2003 | Pearson | .................... | A61J 7/02 221/211 |
| 2004/0112909 | A1 * | 6/2004 | Yamamoto | .............. | B65B 5/103 221/7 |
| 2004/0118753 | A1 * | 6/2004 | Belway | ..................... | A61J 7/02 209/551 |
| 2006/0006048 | A1 * | 1/2006 | Trygar | .................... | B65B 5/103 198/459.1 |
| 2006/0025884 | A1 * | 2/2006 | Henkel | .................... | B65B 5/103 700/216 |
| 2006/0037664 | A1 * | 2/2006 | Monti | ..................... | B65B 35/06 141/129 |
| 2006/0124655 | A1 * | 6/2006 | Ratnakar | .................... | A61J 7/02 221/3 |
| 2006/0124656 | A1 * | 6/2006 | Popovich, Jr. | .......... | G07F 9/026 221/9 |
| 2006/0184271 | A1 * | 8/2006 | Loveless | ................ | A61J 7/0084 700/231 |
| 2008/0092282 | A1 * | 4/2008 | Altmann | ................... | E03D 9/00 4/231 |
| 2009/0281657 | A1 * | 11/2009 | Gak | ......................... | A61J 7/0481 700/242 |
| 2010/0049363 | A1 * | 2/2010 | Ratnakar | ................. | A61J 7/0481 700/236 |
| 2010/0100237 | A1 * | 4/2010 | Ratnakar | ................. | A61J 7/0481 700/232 |
| 2010/0205002 | A1 * | 8/2010 | Chambers | .............. | G06Q 50/22 705/2 |
| 2010/0318218 | A1 * | 12/2010 | Muncy, Jr. | ........... | G06F 19/3462 700/220 |
| 2012/0072017 | A1 * | 3/2012 | Kim | ......................... | B65B 35/14 700/231 |
| 2013/0284755 | A1 * | 10/2013 | Yuyama | ..................... | A61J 7/02 221/13 |
| 2013/0334242 | A1 * | 12/2013 | Yuyama | ..................... | A61J 7/02 221/7 |

(56) References Cited

U.S. PATENT DOCUMENTS

| | | |
|---|---|---|
| 2014/0278510 A1 | 9/2014 | McLean et al. |
| 2014/0361032 A1 | 12/2014 | Czarnek |
| 2015/0175287 A1* | 6/2015 | Tidhar .................... B65B 5/103 700/240 |
| 2016/0167866 A1* | 6/2016 | Omura ................ G07F 17/0092 221/173 |
| 2016/0193113 A1* | 7/2016 | Jacobs .................. A61J 7/0076 221/7 |
| 2017/0224587 A1* | 8/2017 | Koike ................... A61J 7/0084 |
| 2017/0327255 A1* | 11/2017 | Kim ........................ B65B 37/04 |
| 2019/0053986 A1* | 2/2019 | Makhalfeh ............ A61J 7/0481 |

FOREIGN PATENT DOCUMENTS

| | | |
|---|---|---|
| CN | 205034371 U | 2/2016 |
| EP | 2664551 A1 | 11/2013 |
| EP | 2829480 A1 | 1/2015 |
| WO | WO 02/17850 A1 | 3/2002 |
| WO | WO 2009/038378 A2 | 3/2009 |
| WO | WO 2009/137025 A1 | 11/2009 |
| WO | WO 2015/021445 A1 | 2/2015 |

OTHER PUBLICATIONS

Chinese Office Action, dated Feb. 11, 2018, for Chinese Application No. 201510532075.9, with an English translation.
Chinese Office Action, dated Jul. 26, 2017, for Chinese Application No. 201510532075.9, with an English translation.
Chinese Office Action, dated Nov. 28, 2016, for Chinese Application No. 201510532075.9, with an English translation.
Extended European Search Report, dated Jan. 24, 2019, for European Application No. 16838553.2.
Lu, "Packaging Machinery Theory," China Light Industrial Press, May 31, 2011, pp. 272-273 (8 pages total), with an English translation.

* cited by examiner

FULL-AUTOMATIC MEDICATION DISPENSING SYSTEM AND METHOD OF SOLID MEDICATION SEPARATION

CROSS-REFERENCE TO RELATED APPLICATIONS

The present application is a National Stage of International Patent Application No. PCT/CN2016/096308, filed 23 Aug. 2016 which claims foreign priority benefits under 35 U.S.C 119 to Chinese Patent Application No. 201510532075.9 (CN), filed 27 Aug. 2015.

TECHNICAL FIELDS

The present invention relates to the fields of medical devices, automatic medication dispensing technologies, medical mechanical-electrical and information technologies, and particularly relates to a full automatic medication dispensing system and methods of solid medication separation.

BACKGROUND

With the development of science and technologies and the continuous improvement of the medical science, it is necessary for patients to take medications for most of the diseases to be cured or controlled to a certain degree. Due to a variety of reasons, mankind are still faced with the serious problem of not being able to take medication on time and accurately. For patients suffering from many diseases, such as diabetes, cardiovascular diseases, Alzheimer's disease, not being able to take medication on time and accurately can cause very serious negative problems which results in heavy burdens to patients, their families and the society. The New England Healthcare Institute estimates that $290 billion of health care expenditures could be avoided each year if medication adherence were improved in US alone.

As a result, many medication dispensers appear on the market. These dispensers can remind the patients to take medications on time, but these medications need to be manually separated and filled into the dispensers, namely, the medications need to be put into certain boxes one by one in advance, thus the probability of errors and contamination is greatly increased. Meanwhile, along with the increase of the aging society, the self-organizing capacity of the aged is gradually reduced along with the age growth, thus the possibility of errors is even more increased. According to the state-of-art technologies, even the medication dispensing systems in pharmacies, worth of millions of yuans, have to be customized for each single medication based on its size, shape and weight, but very often the medications are jammed when in operation. In addition, the seals of medication boxes of most medication dispensers in the market do not meet the requirements of medication storage, and in some cases there is no seal at all. Very often the parts in contact with medications cannot be cleaned. All those factors can result in premature medication failure and contaminations which will directly affect the health of people taking the medications.

INVENTION

The technical problem mainly solved by the present invention is to provide an automatic dispensing principle through slow feeding and fast discharging in medication flow passages, and create a full-automatic medication dispensing and supply system that can automatically dispense any solid medications and automatically supply medications on time.

To solve the above technical problem, the present invention provides a full automatic medication dispensing system comprising: at least one medication feeding device for containing solid medications, at least one medication separation device for arranging the solid medications into a single line or a column and for opening up the distance between medications, at least one medication distributing channel device for feeding the solid medications exited from the said medication separation device into designated positions, at least one medication supply device for scaling, storing and supplying the medications when need to be taken every time, at least one medication returning device for retrieving and storing surplus medications and at least one central processing unit.

In a preferred embodiment, the said medication feeding device comprises a medication feeding box, wherein the said medication feeding box comprises at least one medication cell and one medication outlet communicated with the said medication separation device, the said medication separation device comprises a medication entrance matched with the said medication outlet, wherein the speed and flow of medications entering the said medication separation device can be effectively controlled by changing the relative positions of said outlet and said entrance.

In a preferred embodiment, the said medication separation device comprises at least one rotary disc or a plurality of concentric rotary discs, and when there are two or more rotary discs, the closer to the outer side, the higher the rotary speed of the said rotary discs, and wherein the said medication separation device further comprises at least one relatively fixed vortex shape medication flow passage above the said rotary disc(s), wherein a vortex outlet is formed at the outer edge of the said vortex shape medication flow passage.

In a preferred embodiment, the said rotary disc further comprises a conical part located at the center of the said rotary disc(s).

In a preferred embodiment, the said vortex shape medication flow passage comprises polygon shape or multiple-arc shape medication flow passages.

In a preferred embodiment, the said medication separation device comprises at least one primary separation body or multi-stage separation bodies, and when the separation bodies are two or more, the medications are separated from top to bottom through a plurality of said separation bodies in sequence, and the separation speed of the said separation body positioned lower is higher than that of the separation body/bodies located above, wherein the separation speed comprises the movement, vibration or rotation speed of the separation body/bodies.

In a preferred embodiment, the said separation body comprises a combination of one or more of a separation box, a separation disc or a conveying belt.

In a preferred embodiment, the said medication separation device comprises at least one rotary disc, two or more relatively fixed vortex passages above the said rotary disc(s), and at least one controllable stiffing plate on the said vortex passage, wherein the number of the said vortex passage is the number of the said rotary disc plus one.

In a preferred embodiment, the said medication separation device comprises at least one rotary disc, at least one shifting fork and more than one actively controlled stiffing plates above the rotary disc, wherein the said shifting fork synchronizes with the stiffing plates, In a preferred embodiment, the said medication distributing channel device comprises a displacement channel located at the lower portion of the said medication distributing channel device, wherein the rotation of the single-degree-of-freedom displacement channel enables medications in the medication distributing channel to fall into different entrances on the upper surface of the said displacement channel leading to the outer cell or inner cell of the medication supply box or the medication retrieving bottle, and the said displacement channel seals the inlet of the said medication supply box after the medication dispensing process is finished.

In a preferred embodiment, the system comprises at least one counting sensor located at the inlet of the said medication distributing channel device and the outlet of the said medication separation device.

In a preferred embodiment, the said medication supply device comprises a medication supply box and a medication taking box, wherein the said medication supply box comprises a cartridge, a plurality of inner cells and outer cells on the said cartridge, wherein the said inner cells and the outer cells are circumferentially distributed on the cartridge, and the outer cells are located on the outer side of the inner cells, and the said medication supply device further comprises a rotary shifting cover plate at the bottom of the said medication supply box, a first outlet and a second outlet corresponding to the said outer cell and the inner cell on the cartridge, wherein the single-degree-of-freedom rotary displacement of the said rotary shifting cover plate can expose the said first outlet or the second outlet of the said medication supply box or seal the two outlets completely, wherein the medication taking box is movably connected to the said medication supply box from below.

In a preferred embodiment, the said medication returning device comprises a fixed disc, a medication retrieving bottle retainer and medication retrieving bottles, wherein at least one medication retrieving bottle can be clamped to the medication retrieving bottle retainer from below, and the said medication retrieving bottle retainer comprises openings above each corresponding medication retrieving bottle, wherein the said medication retrieving bottles can be original medication bottles or marked alternative medication bottles, and wherein the said medication retrieving bottle retainer is movably connected to the said fixed disc.

In a preferred embodiment, the said medication supply device comprises a medication channel, a base, a rotary shaft and a portable medication box, wherein the said rotary shaft is fixed to the lower side of the said fixed disc, the said base is movably connected to the said rotary shaft and can rotate around the said rotary shaft, wherein the portable medication box is movably attached to the said base.

In a preferred embodiment, the said portable medication box comprises a cartridge, an upper cover, a medication taking opening and a medication taking opening cover, wherein the said cartridge comprises an inner ring, medication cells and an outer ring, the said upper cover can be screwed on to the base of the said portable medication box, and the said cartridge can rotate therein, and in the medication taking process the medications in one medication cell are poured out from the said medication taking opening, wherein the said medication taking opening cover is positioned above the medication taking opening.

In a preferred embodiment, the said portable medication box comprises further a display screen, operation buttons and a confirmation button, the said display screen and the operation buttons are fixed inside the said portable medication box, the said display screen can be seen through the transparent upper cover, and the said confirmation button can be directly accessed through a hole on the said upper cover.

In a preferred embodiment, the said portable medication box can be manually filled with medications and programmed by directly touching operation buttons after the said upper cover is unscrewed, and independently used after the said upper cover is screwed back on, the said portable medication box can also be programmed via mobile client or remote client.

In a preferred embodiment, all parts in contact with medications can be conveniently detached and cleaned or opened and cleaned, and can be conveniently mounted together and can not be assembled in a staggered manner.

In a preferred embodiment, the said central processing unit comprises an embedded control device and a communication device for remote communication and programming, wherein the said embedded control device can receive a series sets of medication taking information including the medication taking time, the medication type and the quantity which are directly input into the said embedded control device to control the operations of medication dispensing, medication discharging, reminding and alarming and displaying any error information, the operator can be reminded and required to modify parameters when the set parameters exceed the maximum capacity of the system, and the operator can also be reminded to add a specific medication when the medication is used up in the medication dispensing process, the status of the system just before power outage can be automatically memorized and resumed to continue to run after the power supply is restored, information can also be input via mobile client and/or remote client such as said medication taking information, selected different medication taking reminding modes, people who need to be notified when medications are not taken or more medications and/or medication dispensing are needed, and related information is sent to the personnel in time, whether the set medication dosage is normal or not can also be reminded through the expert system at the remote client site, and the big data related to the medication taking can be collected.

The present invention also provides methods of solid medication automatic separation, wherein the advancing speed of the medications entering the said medication separation device is gradually increased along the medication flow passage in a slow-feeding and fast-discharging mode, the increase of medication advancing speed can be non-continuous and reaches maximum at the outlet of the said medication separation device so that effective separation between the medications is realized.

In a preferred embodiment, movements of medications are realized through part or all of the five factors comprising friction force, centrifugal force, gravity, mechanical stiffing and limit the moving directions in the medication passage.

In a preferred embodiment, the methods of solid medication automatic separation are also suitable for separating solid substances.

The present invention possesses the following advantages:

(1) When medications are processes based on the automatic dispensing principle, structure and methods through slow feeding and fast discharging in medication flow passages, the system has no requirement on the size, shape and weight of any solid medications, namely, as long as the medications are solid, the system can automatically dispense and supply the medications.

(2) The system only requires one time input of a series sets of medication taking time, medication type and quantity to dispense the medications automatically, accurately and efficiently into a sealed medication supply box according to the set parameters, and the excessive medications are automatically returned to the medication retrieving bottles. The system is convenient and safe to use with high accuracy.

(3) When it is time to take medications, the system can remind the medication taking person in time and automatically supply the medications after confirmation. The system can inform preset personnel when a dose of medications are not taken after a preset period of time.

(4) The problem of medication storage in a sealed container is solved because the medication supply box is sealed and the original medication bottles are also sealed after their original covers are put back on.

(5) All parts in contact with medications can be conveniently detached and cleaned or opened and cleaned, and can be conveniently mounted together and can not be assembled in a staggered manner, so that a clean medication dispensing and storage environment is realized.

(6) The fixed medication supply box and the portable medication box meet the requirements of different medication taking people, and the portable medication box can be manually filled with medications and used independently.

(7) The status of the system just before power outage can be automatically resumed to continue to run after the power supply is restored.

(8) The system eliminated the possibility of medication dispensing errors, avoided the possible contamination caused by manual medication dispensing, made the medication dispensing and medication taking process very convenient, greatly increased the proportion of people taking medications on time and accurately, and thus is of great medical, economical and practical value.

DESCRIPTION OF DRAWINGS

Constituting a part of this application, the accompanying drawings are included to provide a further understanding of the invention, exemplary embodiments of the present invention and descriptions thereof are used to explain the present invention, and do not constitute improper limitation to the present invention. In the drawings.

Figure 1:
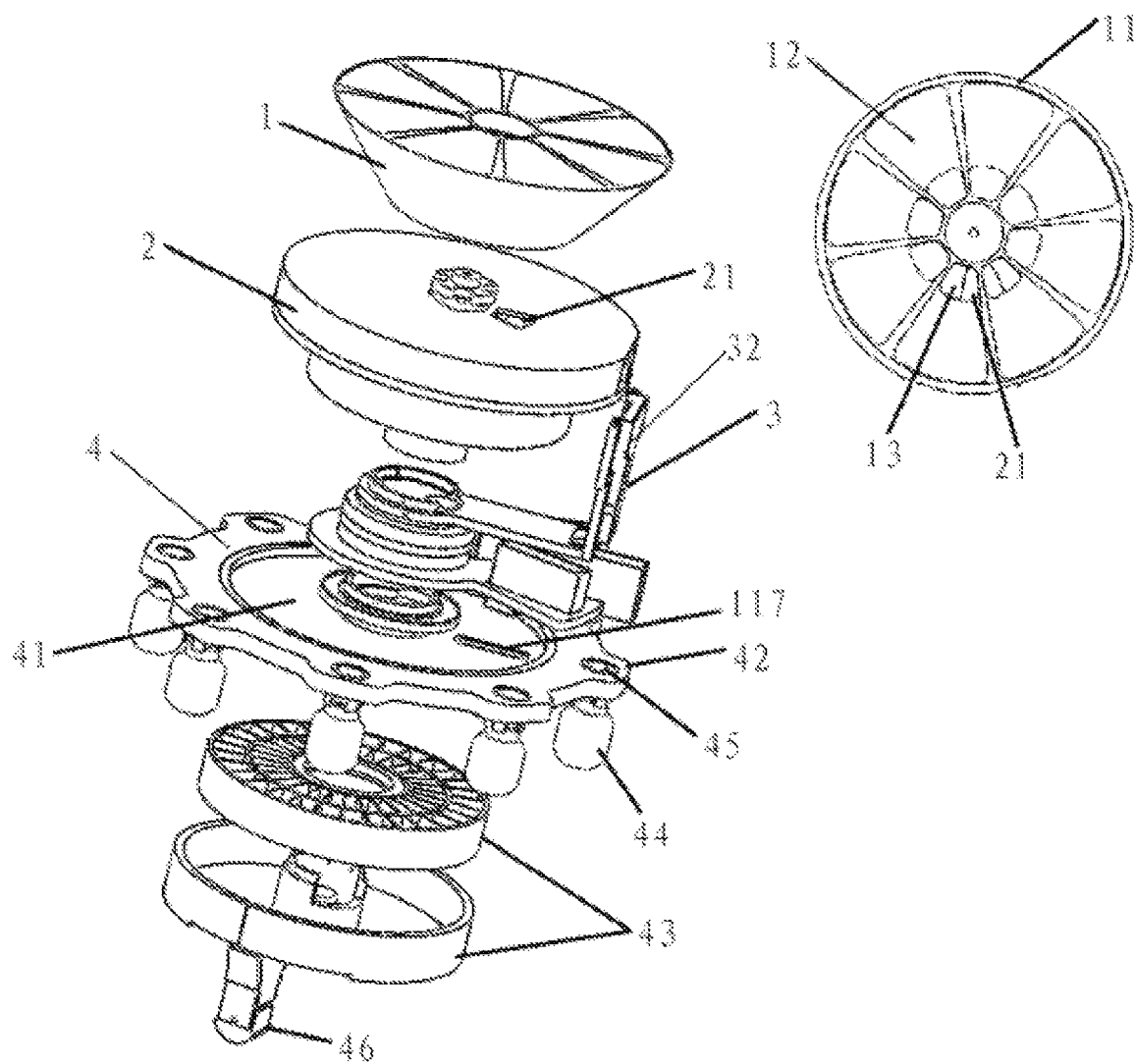
FIG. 1 is a structural diagram of the present invention of a full automatic medication dispensing and supply system of preferred embodiment 1.

Components in the drawings are labeled as follows:

1, medication feeding device; 2, medication separation device; 3, medication distributing channel device; 4, medication returning device; 11, medication feeding box; 12, medication cell; 13, medication outlet; 21, medication entrance; 22, first rotary disc; 23, second rotary disc; 24, vortex shape medication flow passage; 25, vortex outlet; 27, conical part; 29, joint of rotary discs; 31, counting sensor; 32, medication distributing channel; 33, rotary displacement channel; 34, sealing device; 41, fixed disc; 42, medication retrieving bottle retainer; 43, medication supply box; 44, medication retrieving bottle; 45, opening; 46, medication taking box; 117, medication supply box inlet; 121, rotary shaft; 122, base; 123, portable medication box; 124, medication channel; 125, medication taking opening; 126, medication cells; 127, cartridge; 128, medication taking opening cover; 129, confirmation button; 130, upper cover; 131, display screen; 132, operation buttons; 133, inner ring; 134, outer ring; 410, first stage separation box; 411, second stage separation box; 412, third stage separation box; 413, first stage inlet; 414, first stage outlet; 415, second stage inlet; 416, second stage outlet; 417, third stage inlet; 418, third stage outlet; 431, cartridge; 432, inner cells; 433, outer cells; 434, rotary shifting cover plate; 435, first outlet; 436, second outlet; 500, medications; 520, first rotary disc; 521, first passage; 522, second rotary disc; 523, second passage; 524, third rotary disc; 525, third passage; 526, outlet; 529, inlet; 600, medications; 627, first conveying belt; 628, first scraping plate; 629, second conveying belt; 630, second scraping plate; 631, third conveying belt; 632, third scraping plate; 700, medications; 733, rotary disc; 734, inner vortex; 735, rotating shaft; 736, stiffing plate; 737, outer vortex; 800, medications; 838, rotary disc; 839, active shifting fork; 840, first active stiffing plate; 841, first rotary shaft; 842, second active stiffing plate; 843, the second rotary shaft; 844, third active stiffing plate; 845, third rotating shaft; 846, baffle plate; 847, outlet

PREFERRED EMBODIMENTS

The following are preferred embodiments of the technical aspects of the present invention. Obviously, the embodiments are only exemplary of the technical aspects of the present invention, not in their entirety. All other embodiments, obtained by persons of skills in the field from or out of the subject invention without having to put in any creative effort, falls within the protective scope of the present invention.

Preferred Embodiment 1

Referring to FIG. 1-FIG. 6, an embodiment of the present invention comprises of:

A full automatic medication dispensing system comprising: a medication feeding device 1 for containing different types of solid medications, a medication separation device 2 for arranging the solid medications output from said medication feeding device 1 into a single line or a column and for opening up the distance between medications, a medication distributing channel device 3 for feeding the solid medications exited from the said medication separation device 2 into designated positions, a medication supply box 43 for sealing, storing and supplying the medications when need to be taken every time, a medication returning device 4 for retrieving and storing surplus medications and a central processing unit. The said medication feeding device 1 comprises a medication feeding box 11, wherein the said medication feeding box 11 comprises at least one medication cell 12, the number of medication cells 12 in the preferred embodiment 1 is 8, which can, of course, be increased or decreased according to different applications. The said medication feeding box 11 also comprises a medication outlet 13 communicated with the said medication separation device 2. The said medication separation device 2 further comprises a medication entrance 21 matched with the said medication outlet 13. The said medication distributing channel device 3 comprises a fixed counting sensor 31 and medication distributing channel 32. The said medication returning device 4 comprises a fixed disc 41, a medication retrieving bottle retainer 42 and medication retrieving bottles 44, wherein at least one medication retrieving bottle 44 can be clamped to the medication retrieving bottle retainer 42 from below, and the said medication retrieving bottle retainer 42 comprises openings 45 above each corresponding medication retrieving bottle 44, wherein the said medication retrieving bottle retainer 42 and said medication supply box 43 are movably connected to the said fixed disc 41.

Figure 2:
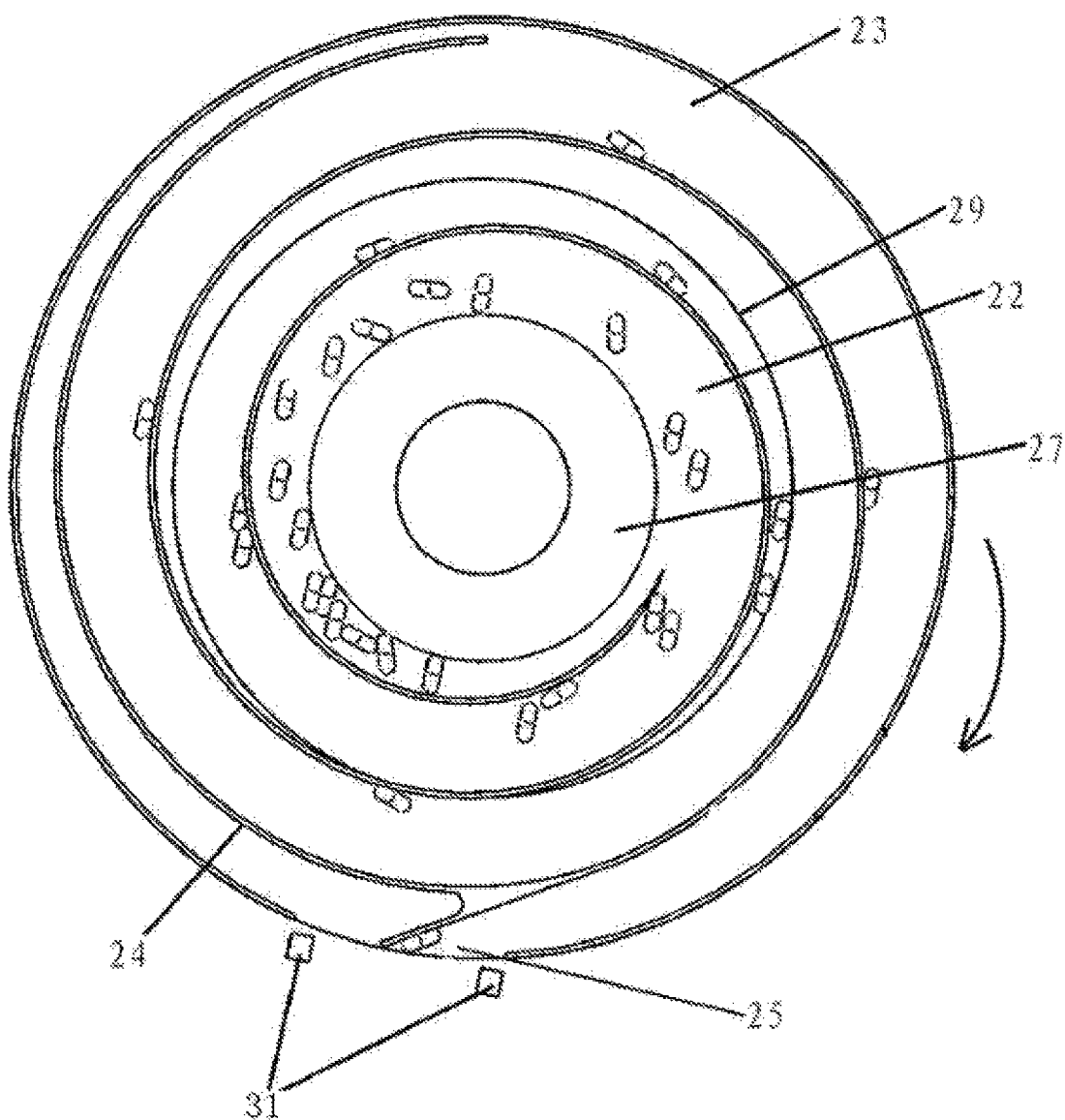
FIG. 2 is a structural diagram of the mediation separation device in FIG. 1.

As shown in FIG. 2, the said medication separation device 2 comprises two rotary concentric rotary discs, namely first rotary disc 22 and second rotary disc 23, and a fixed vortex shape medication flow passage 24 above the said rotary discs, wherein a vortex outlet 25 is formed at the outer edge of the said vortex shape medication flow passage 24. The first rotary disc 22 and the second rotary disc 23 are intersected at the joint 29 of the rotary discs.

The said medication separation device 2 comprises a counting sensor 31 located at said vortex outlet 25 and the inlet of the said medication distributing channel device 32.

The said first rotary disc 22 comprises a conical part 27 located at the center of the said rotary discs.

Figure 3:
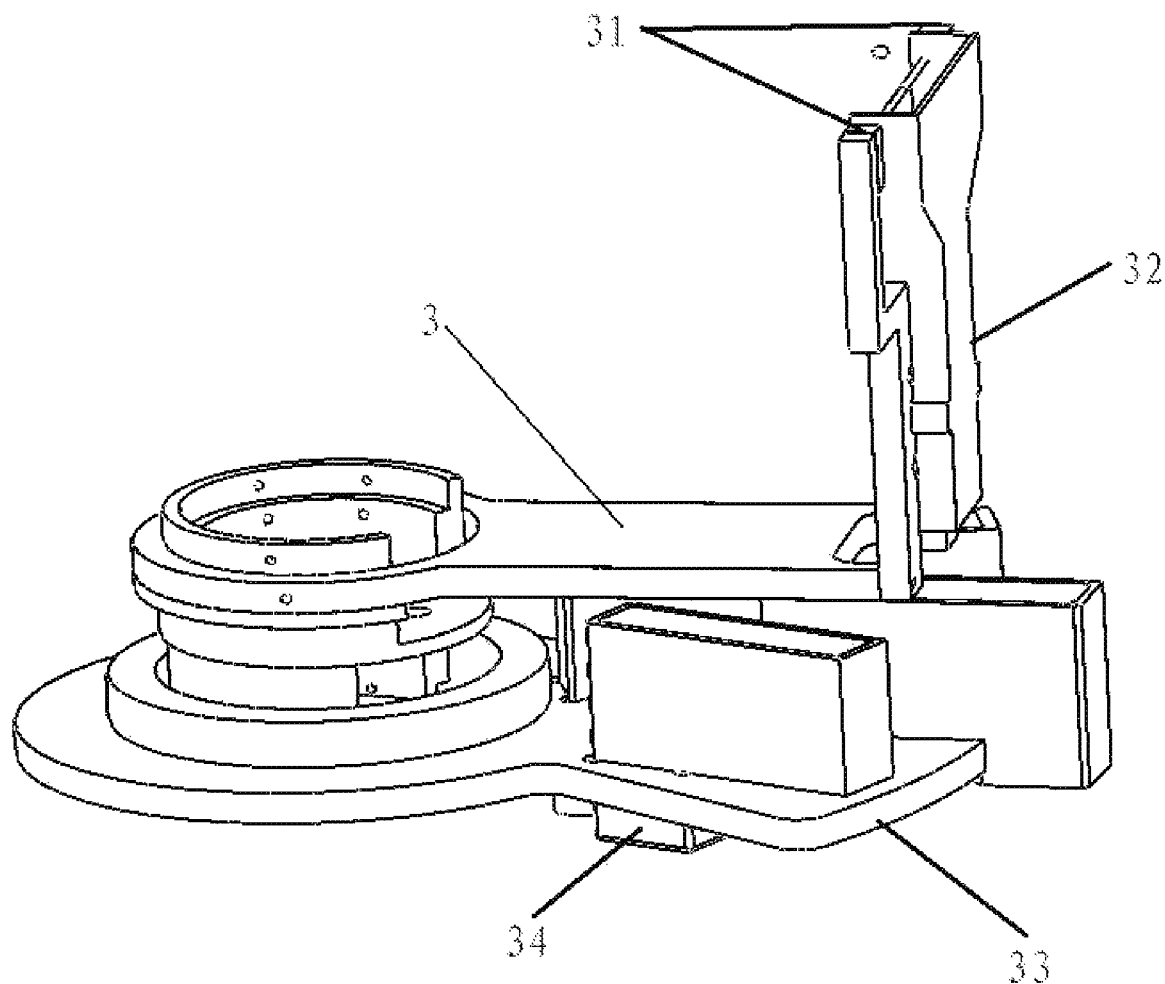
FIG. 3 is a structural diagram of the medication distributing channel device in FIG. 1.

As shown in FIG. 3, the said medication distributing channel device 3 comprises a rotary displacement channel 33, and the said rotary displacement channel 33 is located at the lower portion of the said medication distributing channel device 32, the said rotary displacement channel 33 enables medications in the medication distributing channel 32 to flow through different entrances on the upper surface of the said rotary displacement channel 33 and fall into medication supply box 43 or the medication retrieving bottle 44.

Figure 4:
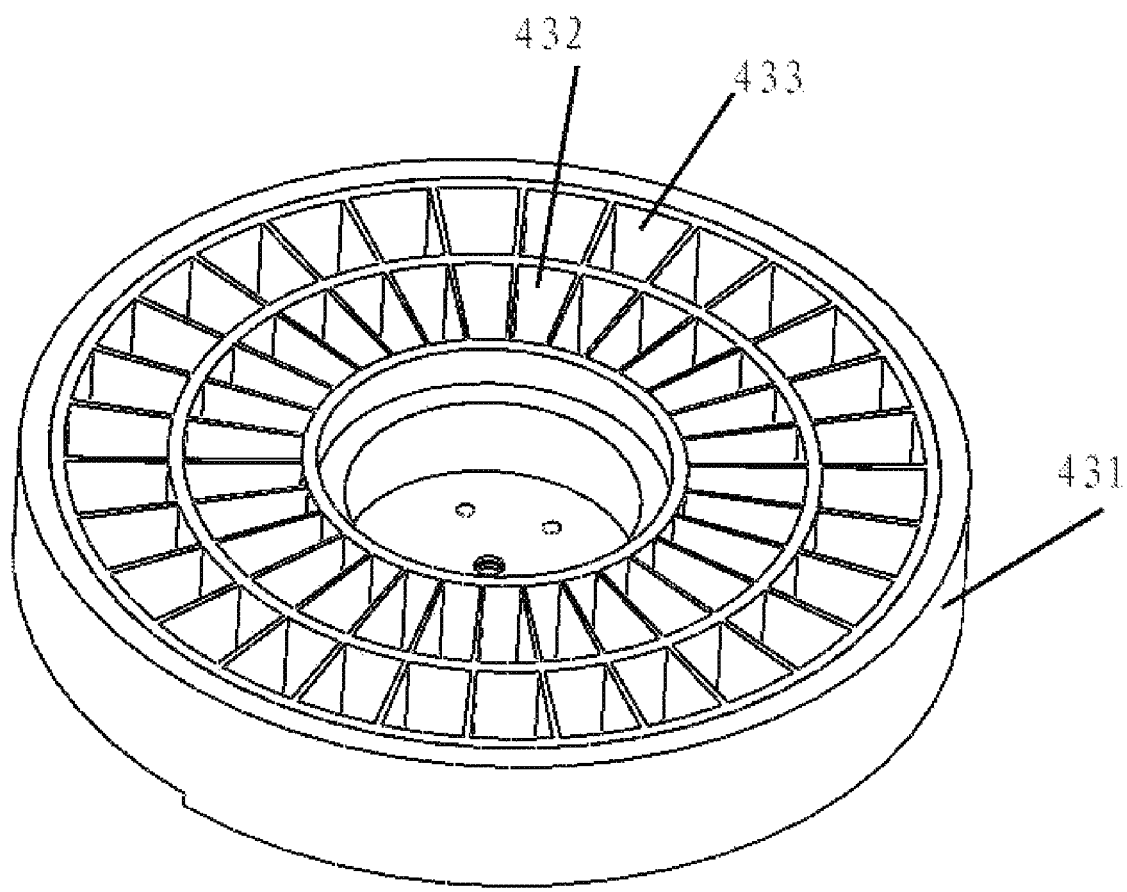
FIG. 4 is a structural diagram of the cartridge of the medication supply box in FIG. 1.

As shown in FIG. 4, the medication supply box 43 comprises a cartridge 431, a plurality of inner cells 432 and outer cells 433 on the said cartridge 431, wherein the said inner cells 432 and outer cells 433 are circumferentially distributed on the said cartridge 431, and the outer cells 433 are located on the outer side of the said inner cells 432. Outlets on the said rotary displacement channel 33 correspond to the radial position of the inner cells 432 and the outer cells 433.

Figure 5:
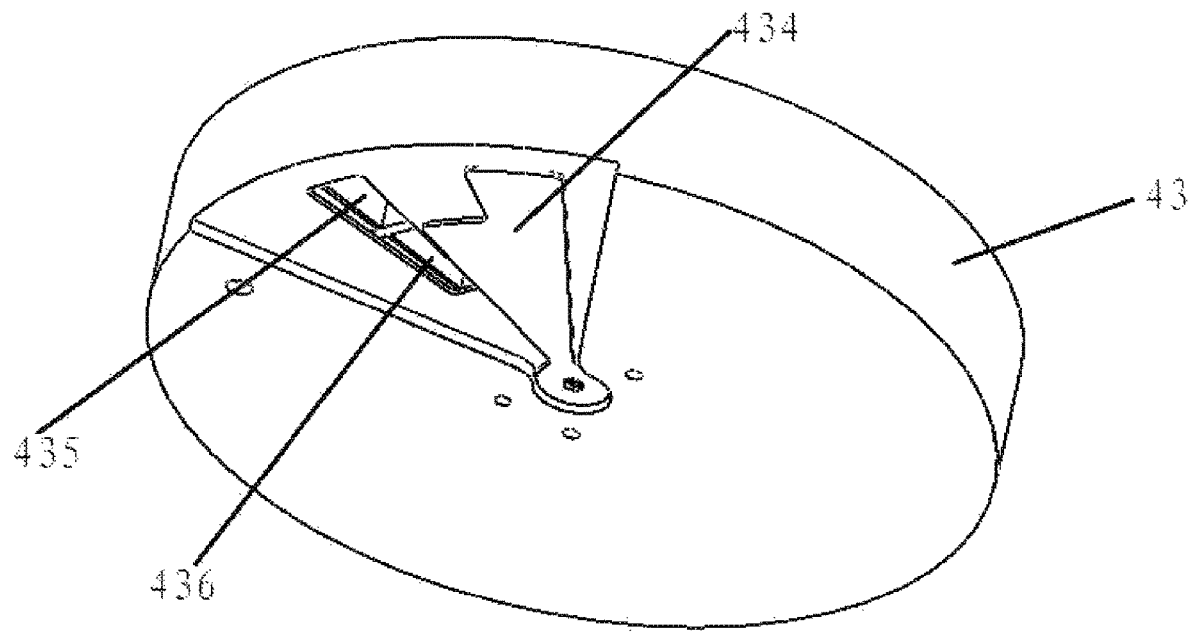
FIG. 5 is a structural diagram of the bottom of medication supply box in FIG. 1.

As shown in FIG. 5, at the bottom of the said medication supply box 43 further comprises a rotary shifting cover plate 434, a first outlet 435 and a second outlet 436, the first outlet 435 and the second outlet 436 are respectively corresponding to the radial positions of the outer cells 433 and the inner cells 432, the said rotary shifting cover plate 434 can expose the first outlet 435 or the second outlet 436 of the said medication supply box 43, so that the medications falls into the medication taking box 46 from the outer cell 433 or the inner cell 432, or the two outlets are simultaneously covered to realize the sealing storage of the medication in the medication supply box 43.

As shown in FIG. 1, the medication supply device 43 further comprises a medication taking box 46, the said medication taking box 46 is movably connected to the said medication supplying box 43 from below.

In addition, the said central processing unit comprises an embedded control device and a communication device for remote communication and programming, wherein the said embedded control device can receive a series sets of medication taking information including the medication taking time, the medication type and the quantity which are directly input into the said embedded control device to control the operations of medication dispensing, medication discharging, reminding and alarming, information can also be input via mobile client and/or remote client such as said medication taking information, selected different medication taking reminding modes, people who need to be notified when medications are not taken or more medications and/or medication dispensing are needed, and related information is sent to the personnel in time, whether the set medication dosage is normal or not can also be reminded through the expert system at the remote client site, and the big data related to the medication taking can be collected.

As shown in FIGS. 1-5, the medication separation device 2 has to be suitable for any solid medication, and there is no requirement on the size, shape and weight of solid medications. Based on the principle of slow feeding and fast discharging in medication flow passages, the medication separation device 2 can arrange solid medications which are disorderly stacked together into a single line or a column, open up the distance between medications, and dispense preset type and quantity of medications to preset destinations through the counting sensor 31 and the medication distributing channel 32.

The operator needs to pour each medication into a medication feeding cell 12 of the medication feeding box 11 from the original medication bottle in sequence, and then the original bottle of the medication (namely medication retrieving bottle 44 in the embodiment) is clamped to the corresponding clamp under the corresponding opening 45 on the medication retrieving bottle retainer 42 from below. If a certain kind of medication is not bottled, a marked alternative medication bottle can be used in replace.

After the medication feeding process is completed, the system is started, by controlling the rotating angle of the medication feeding box 11, the medication in the first cell of medication cells 12 fall through the medication outlet 13 at the bottom into the medication entrance 21 at the upper part of the medication separation device 2 by means of gravity. The relative rotary angle of the medication outlet 13 and the medication entrance 21 is controlled, so that the speed of the medications entering the medication separation device 2 can be effectively increased or reduced, and the flow of the medications can be controlled.

Medications are placed in the medication feeding device 1 from the medication cell 12, and enter the medication separation device 2 through the medication outlet 13 and the medication entrance 21, then fall eccentrically onto the first rotary disc 22 close to the circle center. The first rotary disc 22 drives the medications to move along the diffusion direction of the fixed vortex shape medication flow passage 24 under the action of friction force. As the rotation radius is continuously increased, and the linear speed of each medication is continuously increased, that is, the travel distance in unit time is also continuously increased, therefore the distance between the medications is opened up. When the centrifugal force reaches a certain amount, the medications fall close to the outer side of the vortex shape medication flow passage 24, thus the non-circular medications move forwards along the length direction of the medications. When the speed of the rotary disc is slow, medications stay close to the inner side of the vortex shape medication flow passage 24, thus the non-circular medication moves forwards along the length direction of the medications as well. In this way, medications have been effectively separated at the vortex outlet 25, so that the counting by the counting sensor 31 and the follow-up control of the medication distributing channel are very accurate and reliable, and accurate medication dispensing is realized.

In actual use, if a medication just falls into the center of the first rotary disc 22, the medication might stay in place at the center. To avoid this, a conical part 27 is fixed on the first rotary disc 22 so that medications can only fall to the bottom of the conical part 27, thus medications fall off the center but are still close to the center of the first rotary disc 22.

In order to more effectively separate any type of same medications, the rotary disc can be composed of a plurality of rotary sub-discs, the closer to the outer side, the higher the rotating speed of the rotary sub-discs. The first rotary disc 22 and the second rotary disc 23 are intersected at the joint 29 of the rotary discs, and the speed of the second rotary disc 23 is faster than that of the first rotary disc 22. In the preferred embodiment 1, the number of the rotary discs is two, according to the actual use conditions, the rotary disc can be one or more concentric discs, as long as the rotating speed of the rotary disc close to the medication inlet is the lowest, and that close to the medication outlet is the highest and gradually increases.

Medications are completely discharged into a row or a column through the medication separation device 2 and are pulled away from each other, moved through a counting sensor 31 and a medication distributing channel 32 at the upper side of the medication distributing channel device 3, then the medications fall into the outer cell 433 or the inner cell 432 of the medication supply box 43 according to the control logic by rotating the rotary displacement channel 33 below the medication distributing channel 32, and excessive medications are loaded to medication retrieving bottle 44 through the corresponding opening 45 on the medication retrieving bottle retainer 42. Of course the cartridge 431 of the medication supply box 43 also needs to rotate corresponding rotary displacement according to the medication taking time and quantity of the medication. After the first type of medications is dispensed, the remaining medications are loaded into the medication retrieving bottle 44 through the opening 45. Then the rotary displacement channel 33 moves to the next dispensing position, the medication retrieving bottle retainer 42 rotates to next station where next medication retrieving bottle 44 is aligned with the corresponding position of the rotary displacement channel 33. The medication feeding box 11 rotates to the next medication cell 12, and similarly, the relative rotary angle of the medication outlet 13 and the medication entrance 21 is controlled, so that the speed of the medications entering the medication separation device 2 can be effectively increased or reduced, and the flow of the medications can be controlled. Thus the dispensing process of the second medication begins.

In this way, all the required medication dispensing can be completed. After all the medication dispensing is done, the operator needs to sequentially take down the medication retrieving bottles 44, put original covers back on corresponding bottles and reserve the medications for next use. The rotary displacement channel 33 rotates to enable the sealing device 34 on the rotary displacement channel 33 to seal the medication supply box inlet 117 on the fixed disc 41. Dynamic seals are used between the upper portion of the medication supply box 43 and the fixed disc 41, and the bottom of the medication supply box 43 is covered and sealed through the rotary shifting cover plate 434. Therefore, the complete sealing of the medication supply box is realized, and the problem of medication storage in a sealed environment is solved.

In the medication dispensing process, if the quantity of certain medications is not enough, the system can remind the operator to add the medication, and continue to operate after the confirmation key is pressed.

After the medication dispensing process is completed, each cell of the inner cells 432 and the outer cells 433 of the medication supply box 43 has an accurate dose of one-time medications, and is arranged in sequence according to the medication taking sequence. The system reminds the medication taking person on time based on the one-time input of a series of medication taking time, medication type and the quantity during the medication dispensing process. When confirmed by the medication taking person, the rotary shifting cover plate 434 rotates one station from the scaling position to expose the first outlet 435 of the supply box 43, thus the first dose of the medications in the outer cell 433 falls into the medication taking box 46, the medication taking person can conveniently take the medication, and the rotary shifting cover plate 434 returns to the sealing position. During the supply of second dose of medications, the rotary shifting cover plate 434 rotates one station from the sealing position, now the outer cell 433 is hollow, the cartridge 431 is required to rotate one station, and the second dose of medication falls into the medication taking box 46, and so on. After all dose of medications in outer cells 433 are supplied, the rotary shifting cover plate 434 rotates two stations from the sealing position to expose the second outlet 436 of the medication supply box 43, and a dose of medications in the inner cell 432 falls into the medication taking box 46, the medication taking person can conveniently take the medications, and the rotary shifting cover plate 434 returns to the sealing position. During the supply of next dose of medications, the rotary shifting cover plate 434 rotates two stations from the sealing position, now the inner cell 432 is hollow, the cartridge 431 is required to rotate one station and the next dose of medications falls into the medication taking box 46, the medication taking person can conveniently take the medications, the rotary shifting cover plate 434 returns to the sealing position, and so on.

Apparently, the medication dispensing and supply system has its limitations: the maximum types of medications to be dispensed and supplied must be less than or equal to the number of medication cells 12. In the preferred embodiment 1, the number of the single medication loading cells is 8, namely, at most eight kinds of solid medications can be processed by the system. The number of medication doses of the system must be less than or equal to the total number of the inner cells 432 and the outer cells 433. In the preferred embodiment 1, there are 60 cells in total in the medication supply box 43, that is, the system can process 60 doses of medications at most. Of course these parameters can be increased or decreased according to actual requirements. When the parameters set by the operator exceed the maximum capacity, the system can remind and require the operator to modify.

The system can dispense a plurality of days of medications in one time, the medication taking person only needs to press the confirmation button when being reminded, and the system can automatically supply an accurate dose of medications for the person to take. The reminding information can be displayed on the screen, meanwhile, sound and/or flashing light reminding can be added when the medication taking information is input. After each medication taking, the system can display the number of remaining medication taking times, and when the remaining amount is smaller than a preset value, the system can remind the preset personnel to get more medications on time. The medication dispensing operator can be a reliable relative, a friend or a caregiver of the medication taking person who only needs to dispense medications at regular intervals. For example, when there are 60 cells in the medication supplying box and medications are taken twice daily, only one dispensing is needed every 30 days. This is a great news for medication taking people whose intelligence is reduced, actions are limited or inconvenienced and who are aged and the like, especially for people who take medications at home.

Figure 6:
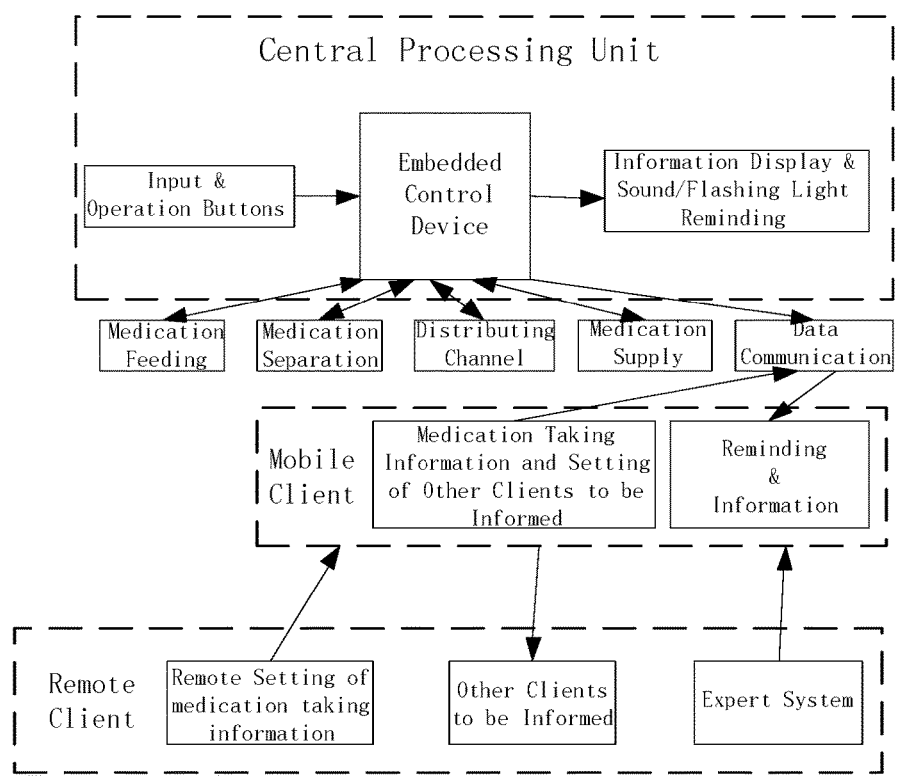
FIG. 6 is a relationship diagram of a full automatic medication dispensing and supply system with a fixed medication supply box of preferred embodiment 1.

To meet more advanced requirements of some users, as shown in FIG. 6, the medication dispensing and supply system can also communicate with selected mobile client through bluetooth or wi-fi, the operator can conveniently input the medication taking information through the powerful touch screen interface of the smart mobile device, select different medication taking reminding modes, preset personnel to be informed when a dose of medication is not taken or more medications and/or medication dispensing are needed, set up connection with remote client and authorize the remote system setup, get the reminds from the remote expert system on whether the dosage of each medication and combinations of all medications are normal or not. Big data related to the medication taking can be collected. Even when the system is not by the side of the medication taking person, the mobile device can still be around the medication taking person. System reminding, mobile device reminding or both can be selected during system setup. When a dose of medication is not taken after the system reminds the medication taking person for a preset period of time, the system can notify preset personnel. If the next medication taking time is approaching while the dose of medications is still not taken, the system waits for the operator to decide whether to neglect the reminder and take the dose in sequence or discharge the dose of medications. When the number of the remaining medication taking times is smaller than a preset value, the system can notify preset personnel to get more medications on time and the date and time of the next medication dispensing. When needed, medications in the system can also be taken in advance by pressing the corresponding button.

The system can display any error information in time. In case of a sudden power outage, the system can resume to continuously run from the status before the power outage after the power supply is restored.

Preferred Embodiment 2

Figure 7:
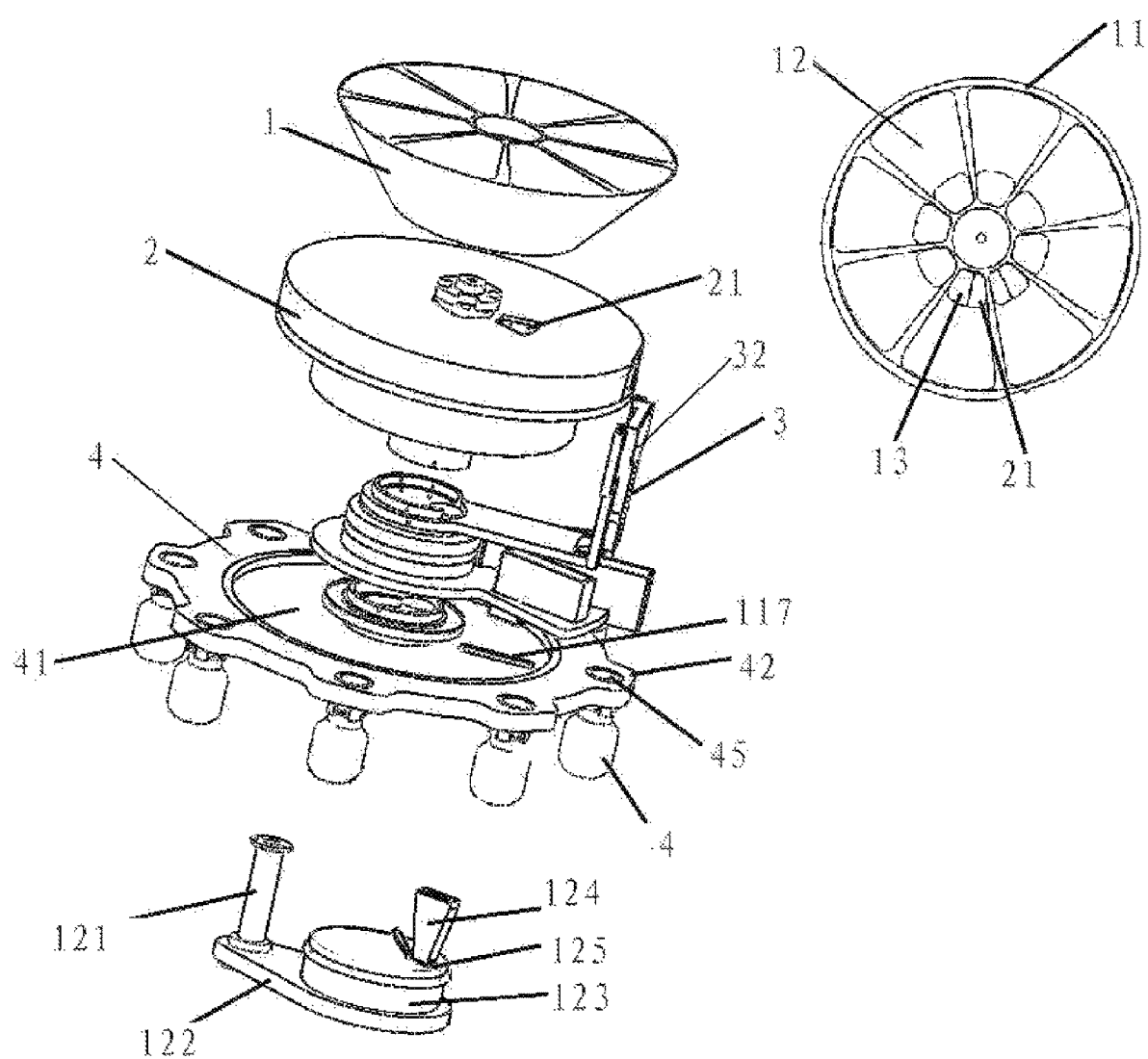
FIG. 7 is a structural diagram of the present invention of a full automatic medication dispensing and supply system of preferred embodiment 2.
Figure 8:
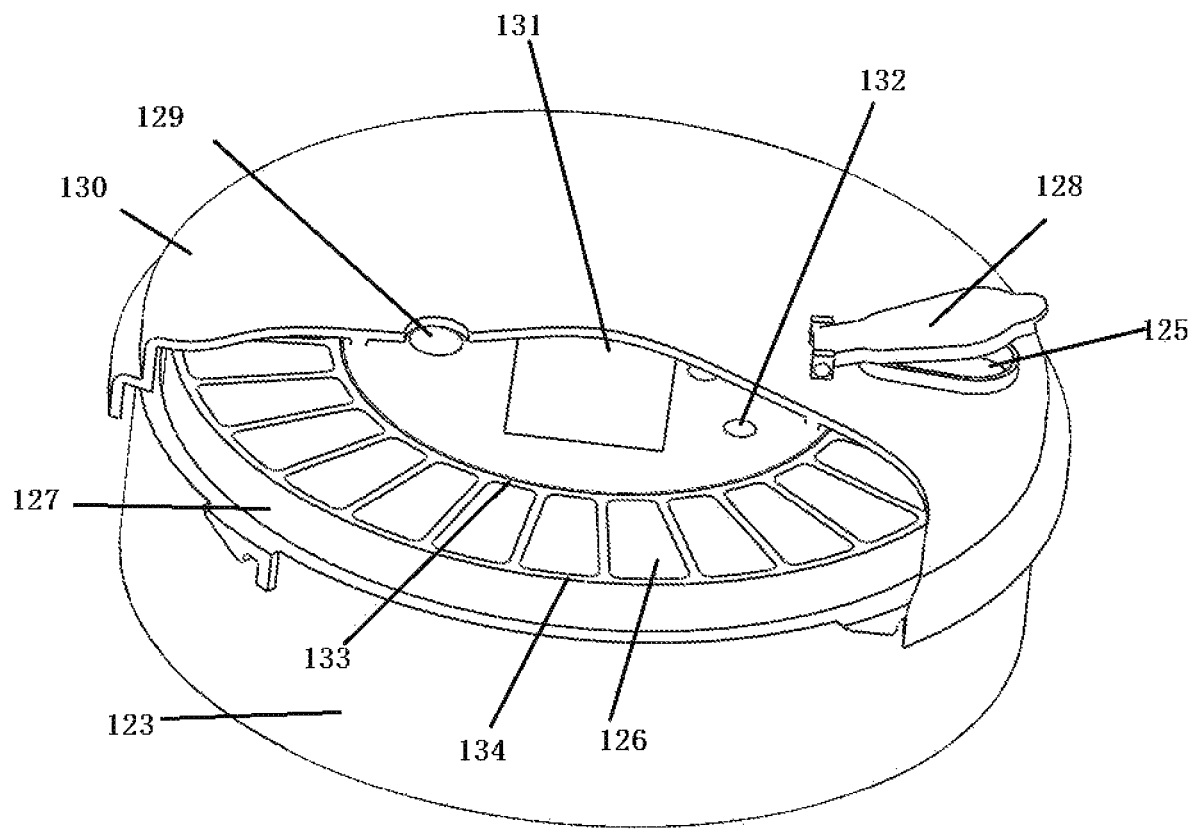
FIG. 8 is a structural diagram of the portable medication box in FIG. 7.
Figure 9:
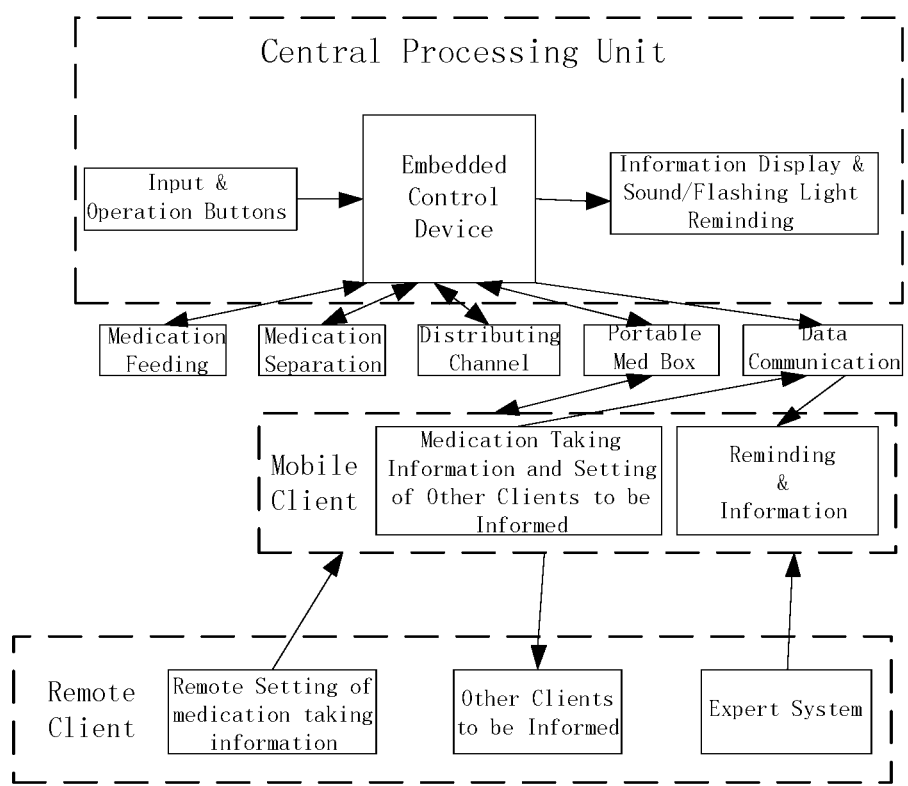
FIG. 9 is a relationship diagram of a full automatic medication dispensing and supply system with a portable medication supply box of preferred embodiment 2.

Referring to FIG. 7 to FIG. 9, the present embodiment differs from the preferred embodiment 1 in that the medication supplying box in the preferred embodiment 1 is a fixed medication box and the medication supply box in the preferred embodiment 2 is a portable medication box which is particularly suitable for people who take medications at work, during business trips and travels and the like.

Detailed structure of the said portable medication box is as follows: the medication supply box comprises a base 122, a rotary shaft 121 and a portable medication box 123, wherein the said rotary shaft 121 is fixed to the lower side of the fixed disc 41, the base 122 is movably connected to the rotary shaft 121 and can rotate around the rotary shaft 121, wherein the portable medication box 123 is movably attached to the base 122.

As shown in FIG. 8, the portable medication box 123 comprises a cartridge 127, an upper cover 130, a medication taking opening 125 and a medication taking opening cover 128, wherein the said cartridge 127 comprises an inner ring 133, medication cells 126 and an outer ring 134, the said upper cover 130 can be screwed on to the base of the portable medication box 123, and the said cartridge 127 can rotate therein, and in the medication taking process the medications in one medication cell 126 are poured out from the medication taking opening 125, wherein the medication taking opening cover 128 is positioned above the medication taking opening 125.

In addition, the portable medication box 123 comprises further a display screen 131, operation buttons 132 and a confirmation button 129, the said display screen 131 and the operation buttons 132 are fixed inside the portable medication box 123, the said display screen 131 can be seen through the transparent upper cover 130, the upper cover 130 needs to be unscrewed only when the said portable medication box 123 is manually filled with medications and programmed by directly touching the operation buttons 132, and the confirmation button 129 can be directly accessed through a hole on the upper cover 130.

The principle of medication dispensing and supply is the same while the difference is in the medication supply boxes. As shown in FIG. 7, a rotary shaft 121 is fixed to the lower surface of the fixed disc 41, and one end of the base 122 can rotate around the axis of rotary shaft 121. The medication channel 124 is clamped below the fixed disc 41 corresponding to the medication supply box inlet 117. The base 122 is first rotated to an outside position, the portable medication box 123 can be conveniently clamped on the base 122 and electrically connected with the system through clamping grooves, then the medication taking opening cover 128 of the medication taking opening 125 is opened, and the base 122 is rotated to the inside position where the medication taking opening 125 and the medication channel 124 are aligned. During the medication dispensing process, medications flow through the medication supply box inlet 117 on the upper surface of the fixed disc 41, the medication channel 124 and the opened medication taking opening 125 of the portable medication box 123, and enter the medication cells 126 of the portable medication box 123. The cartridge 127 of the portable medication box 123 also correspondingly rotates according to the control logic, all other processes are the same as the preferred embodiment 1, except that the number of medication cells of the portable medication box 123 is much smaller than that of a fix medication box in consideration of volume and weight, namely the number of doses is far less than that of a fixed medication box. There are 28 medication cells on the portable medication box 123 in the preferred embodiment 2, which can provide about one week's doses for most medication taking people. The one time input of a series of medication taking time, medication type and quantity and other information for medication dispensing can be transmitted to the portable medication box 123. After the medication dispensing process, the operator rotates the base 122 to an outside position, takes out the portable medication box 123, puts back the medication taking opening cover 128 to seal the medication taking opening 125. There are dynamic seal rings between the upper cover 130 of the medication box 123 and the top of inner ring 133 and the outer ring 134 of the cartridge 127. If a rechargeable battery is used in the portable medication box 123, the base 122 can also charge battery.

When the medications need to be taken, the portable medication box 123 reminds the medication taking person on time, and relevant information is displayed on the display screen 131, meanwhile, the prompt of the sound and/or the flashing light added when the medication taking information was input can appear, the user can see the display screen 131 through the transparent upper cover 130. After the confirmation button 129 is pressed, the medication cell of the portable medication box 123 filled with the medications to be taken is rotated to the position of the medication taking opening 125, the medication taking person opens up the medication taking opening cover 128, pour out the medications in the cell, close the medication taking opening cover 128, so that on time and accurate medication taking is realized.

Similarly, to meet higher requirements of some users, as shown in FIGS. 7-9, the information input and system settings are the same as those of the fixed medication box system in the preferred embodiment 1, all information can be transmitted to the portable medication box, and after the medication dispensing is finished, the mobile client communicate with the portable medication box, all other functions are the same. The system also allows the medications be taken in advance when needed after the button 129 is pressed.

Under the automatic medication dispensing mode, only the confirmation/advance medication taking button 129 on the portable medication box 123 can be accessed from outside. In special situations, the user can select manual dispensing according to the following process: screws and opens the upper cover 130 to expose the cartridge 127 and the operation buttons 132, inputs the medication taking time, the type and the quantity using the operation buttons 132 and the confirmation button 129. When input is completed the display screen 131 can indicate the quantity of the first type of medication and the position of the medication cell, the dispensing of first type of medications is finished when the confirmation button 129 is pressed, and manual dispensing of the second type of medication is started until the operation is completed. The upper cover 130 is screwed back onto the portable medication box 123 and make sure that the medication taking opening cover 128 is closed, all other functions of the portable medication box are the same after the system started. Similarly, the settings of the portable medication box can be completed through a mobile client. Therefore, if manual dispensing is selected, the portable medication box can be independently used.

The medication dispensing and supply systems in the preferred embodiment 1 and the preferred embodiment 2 eliminated the possibility of medication dispensing errors, and avoided the possible contamination caused by manual medication dispensing because the operator's hands do not need to contact with medications. All parts in contact with medications can be conveniently detached and cleaned or opened and cleaned, and can be conveniently mounted together and can not be assembled in a staggered manner. Therefore a clean medication dispensing and storage environment is realized.

Preferred Embodiment 3

Figure 10:
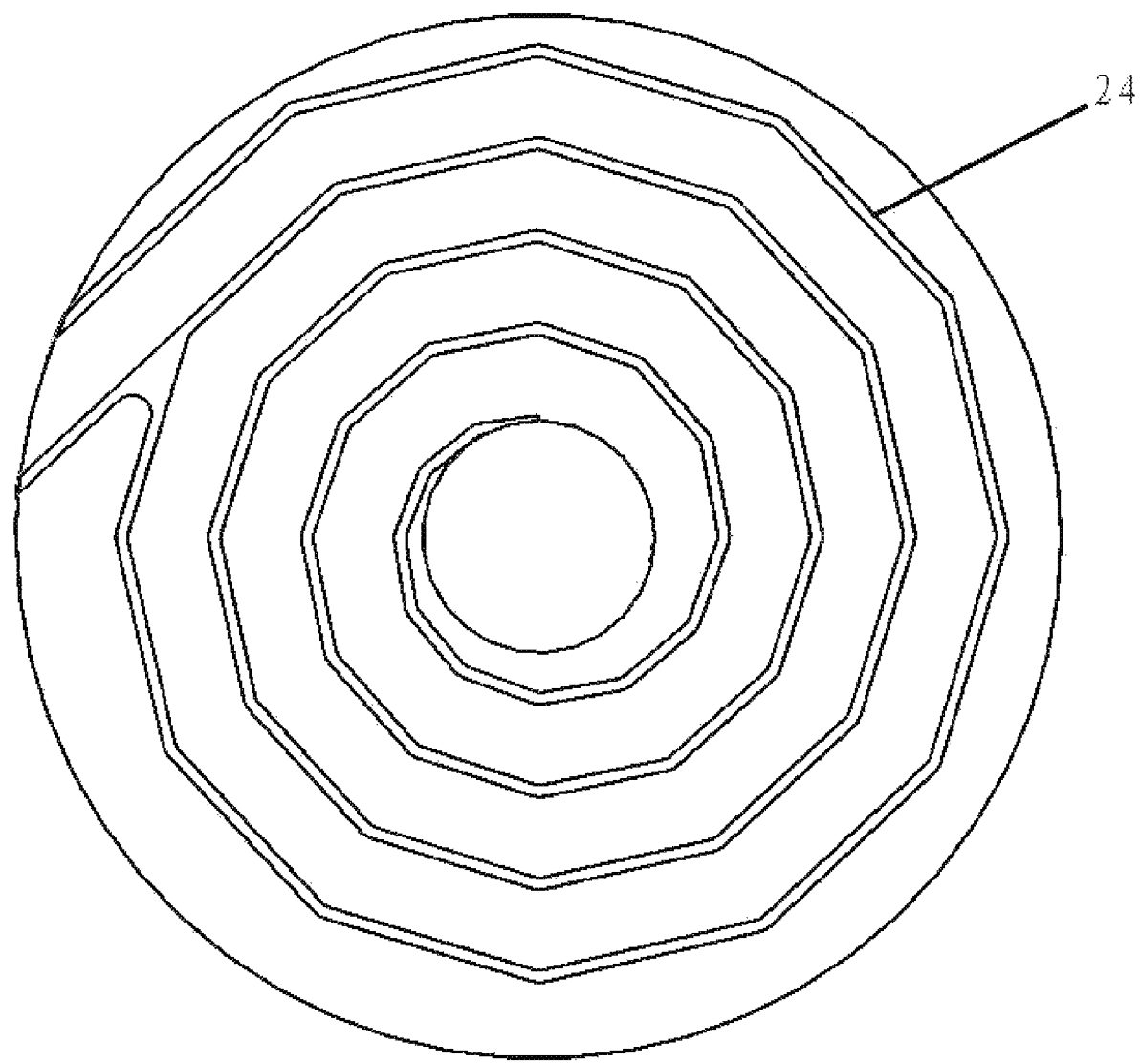
FIG. 10 is a structural diagram of the vortex-like medication flow passage of preferred embodiment 3.

As shown in FIG. 10, the difference between the preferred embodiment 3 and the preferred embodiment 1 is that the vortex shape medication channel 24 can also be composed of polygon shape. The working principle of the device is the same as that of the preferred embodiment 1, and is not repeated herein.

Preferred Embodiment 4

Figure 11:
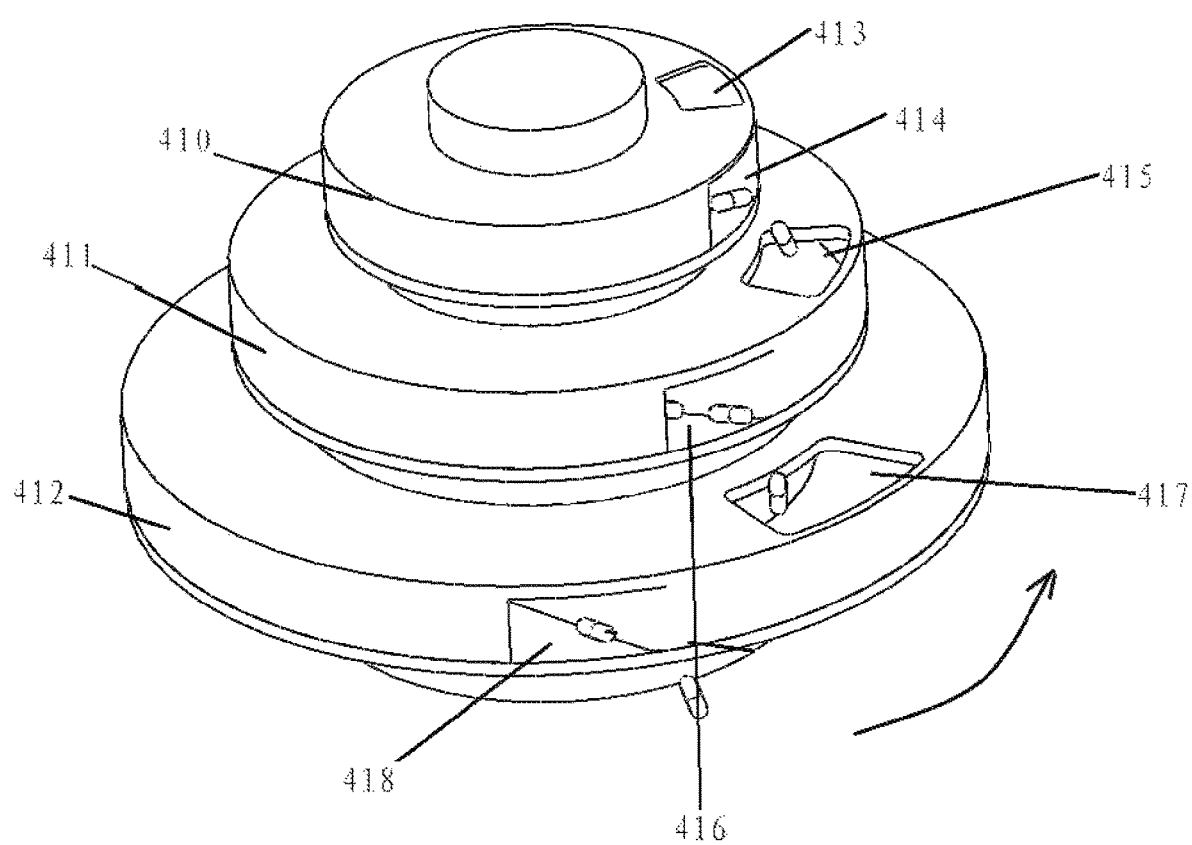
FIG. 11 is a structural diagram of the multi-medication separation bodies of preferred embodiment 4.

As shown in FIG. 11, the difference between the preferred embodiment 4 and the preferred embodiment 1 is that the medication separation device comprises of at least two stages of separation bodies, the medications are separated from top to bottom through a plurality of said separation bodies in sequence, and the separation speed of the said separation body positioned lower is higher than that of the separation body/bodies located above, wherein the separation speed comprises the vibration or rotation speed of the separation body/bodies.

The medication separation device in the preferred embodiment 4 comprises of three-stage separation bodies, the said separation bodies are separation boxes. The three-stage separation bodies comprise of a first-stage separation body, a second-stage separation body and a third-stage separation body which are sequentially connected from top to bottom, wherein each separation body comprises of an inlet and an outlet. Medications enter the inlet and rotate out of the outlet of the first separation body, automatically enter the inlet and rotate out of the outlet of the second separation body, then automatically enter the inlet and rotate out of the third separation body. The rotation speed of the second-stage separation is faster than that of the first-stage separation, and the rotation speed of the third-stage separation is faster than that of the second-stage separation.

As shown in FIG. 11, the principle of "slow feeding and fast discharging" is realized through a three-stage separation boxes. Medications enter the first stage inlet 413 and rotate out of the first stage outlet 414 of the first stage separation box 410, and automatically enter the second stage inlet 415 and rotate out of the second stage outlet 416 of the second stage separation box 411, then automatically enter the third stage inlet 417 and rotate out of the third stage outlet 418 of the third stage separation box 412. The rotation speed of the second stage separation box 411 is faster than that of the first stage separation box 410, and the rotation speed of the third stage separation box 412 is faster than that of the second stage separation box 411. Thus, the distance between medications is effectively opened up, and accurate medication dispensing is realized.

Certainly, in actual applications, each stage of separation body can adopt the combination of a fixed vortex shape medication flow passage and a rotary disc, can also simply be a rotary disc. The driving of the multi-stage separation at different rotation speeds can be achieved by one motor plus different gear transmission ratios. All other principles are the same as that of the preferred embodiment 1 and preferred embodiment 2, and are not repeated herein.

Preferred Embodiment 5

Figure 12:
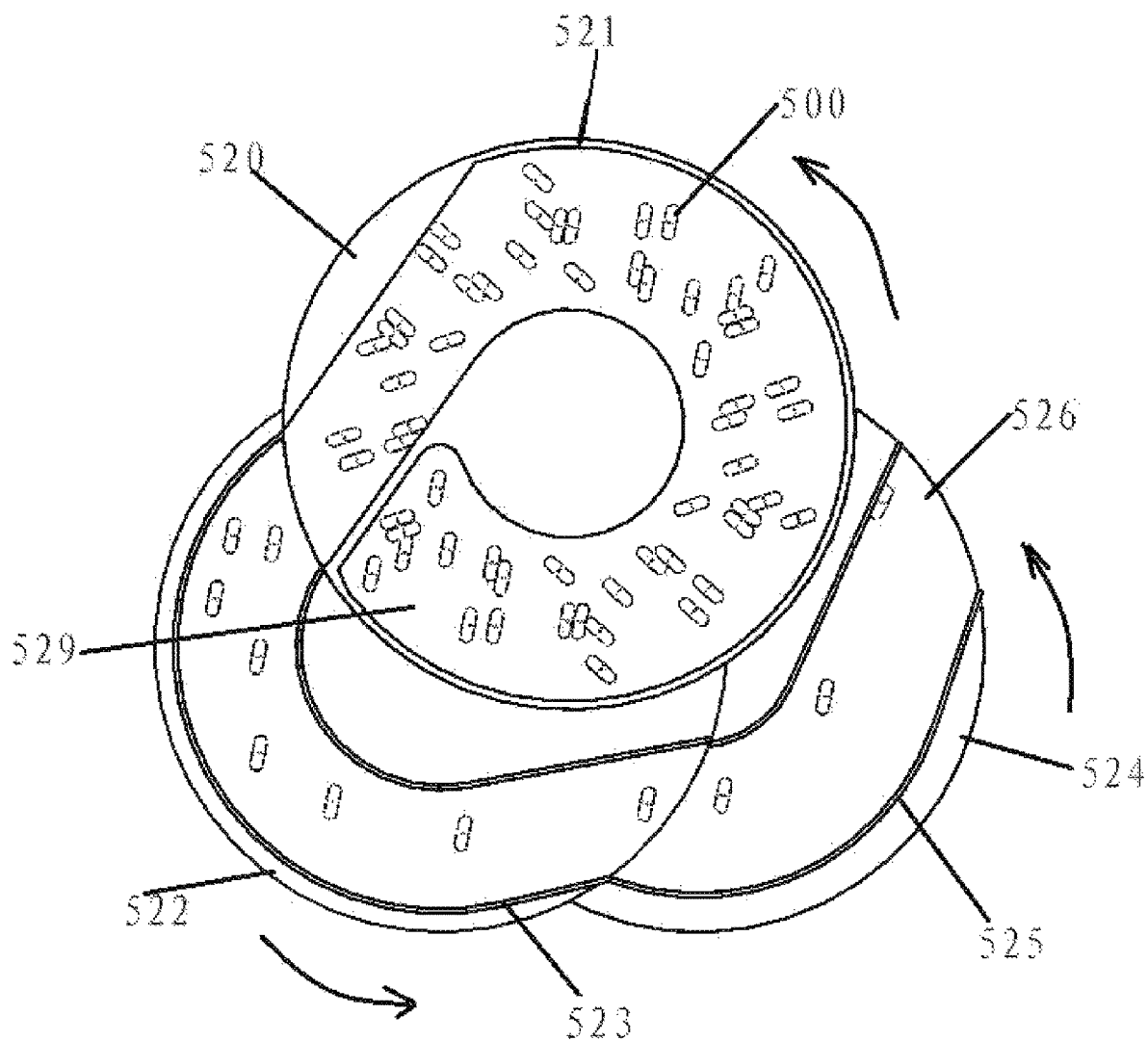
FIG. 12 is a structural diagram of the multi-medication separation bodies of preferred embodiment 5.

As shown in FIG. 12, the difference between the preferred embodiment 5 and the preferred embodiment 4 is that the medication separation device comprises of a three stage separation bodies, the said separation bodies are separation discs. As shown in FIG. 12, medications 500 enter at the inlet 529 of the first rotary disc 520, driven by the first rotary disc 520 to fall by gravity on to the second rotary disc 522 along the first passage 521, driven by the second rotary disc 522 to fall by gravity on to the third rotary disc 524 along second passage 523, driven by the third rotary disc 524 to move forward to the outlet 526 along the third passage 525. The rotating speed of the first rotary disc 520 is the slowest, the rotating speed of the second rotary disc 522 is faster than that of the first rotary disc 520, and so on. Therefore, the distance between medications 500 can be effectively opened up, thus accurate medication dispensing can be realized. Similarly, the driving of the multi-stage rotary discs at different rotating speeds can be achieved by one motor plus different gear transmission ratios. All other principles are the same as that of the preferred embodiment 4, and are not repeated herein.

Preferred Embodiment 6

Figure 13:
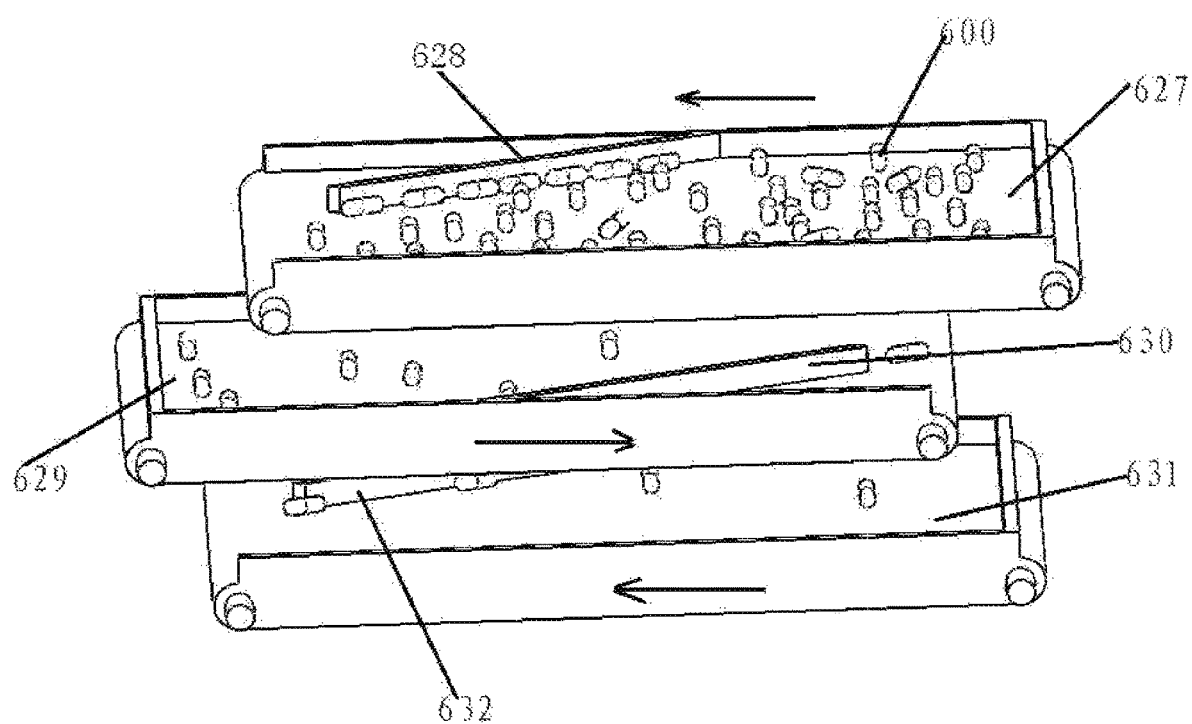
FIG. 13 is a structural diagram of the multi-medication separation bodies of preferred embodiment 6.

As shown in FIG. 13, the difference between the preferred embodiment 6 and the preferred embodiment 4 is that the medication separation device comprises of a three stage separation bodies, the said separation bodies are conveying belts, As shown in FIG. 12, medications 600 enter at front part of the first conveying belt 627, driven by the first conveying belt 627 to move forward and orderly under the action of the first scraping plate 628 until the end of the first conveying belt 627, then fall by gravity on to the second conveying belt 629, driven by the second conveying belt 629 to move forward and orderly under the action of the second scraping plate 630 until the end of the second conveying belt 629, then fall by gravity on to the third conveying belt 631, driven by the third conveying belt 631 to move forward and orderly under the action of the third scraping plate 632 until the outlet. The speed of the first conveyor belt 627 is the slowest, the speed of the second conveyor belt 629 is faster than that of the first conveyor belt 627, and so on. Therefore, the distance between medications can be effectively opened up, thus accurate medication dispensing can be realized. All other principles are the same as that of the preferred embodiment 4, and are not repeated herein.

Preferred Embodiment 7

Figure 14:
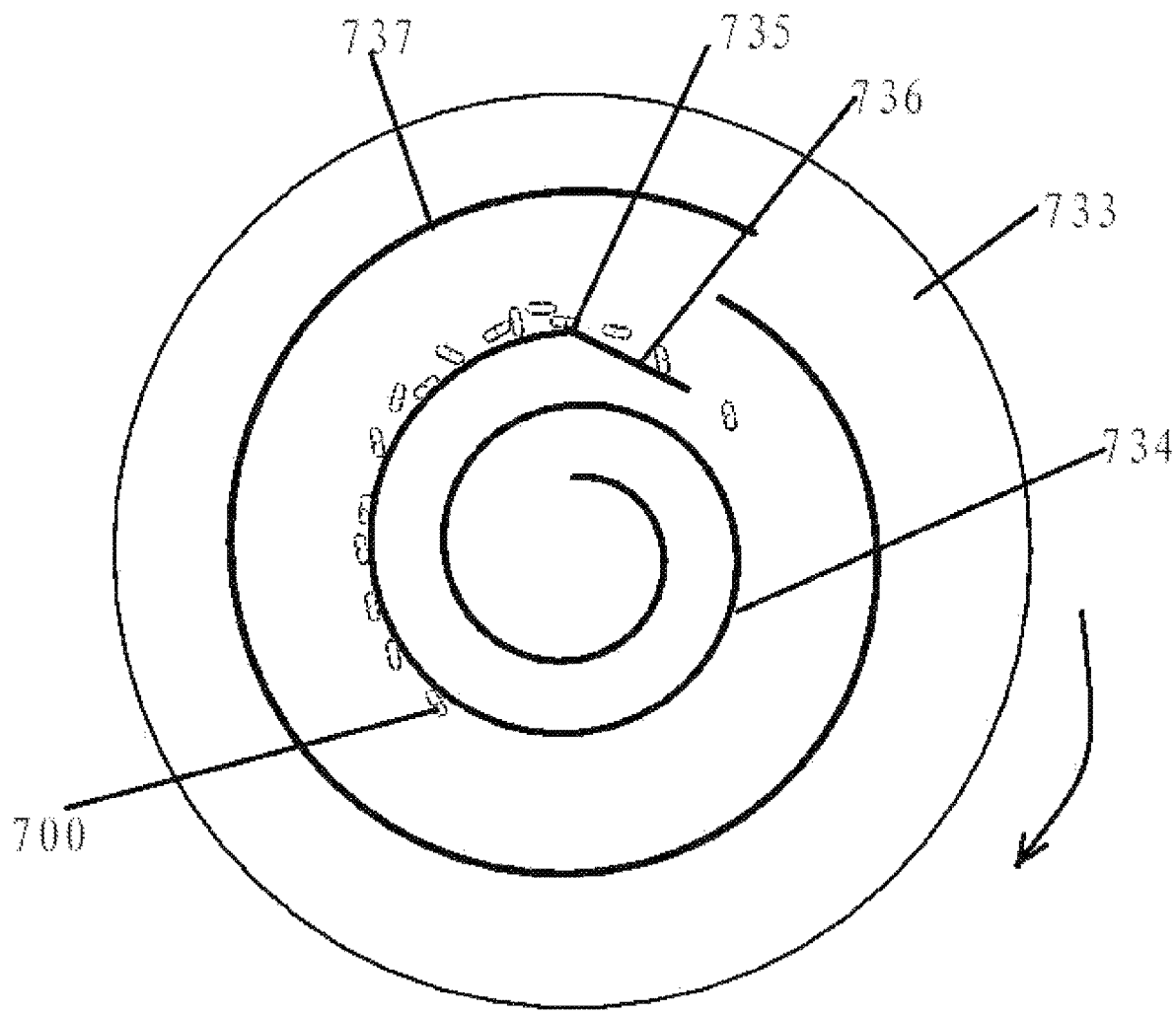
FIG. 14 is a structural diagram of the vortex medication flow passages and mechanical stiffing plate of preferred embodiment 7.
Figure 15:
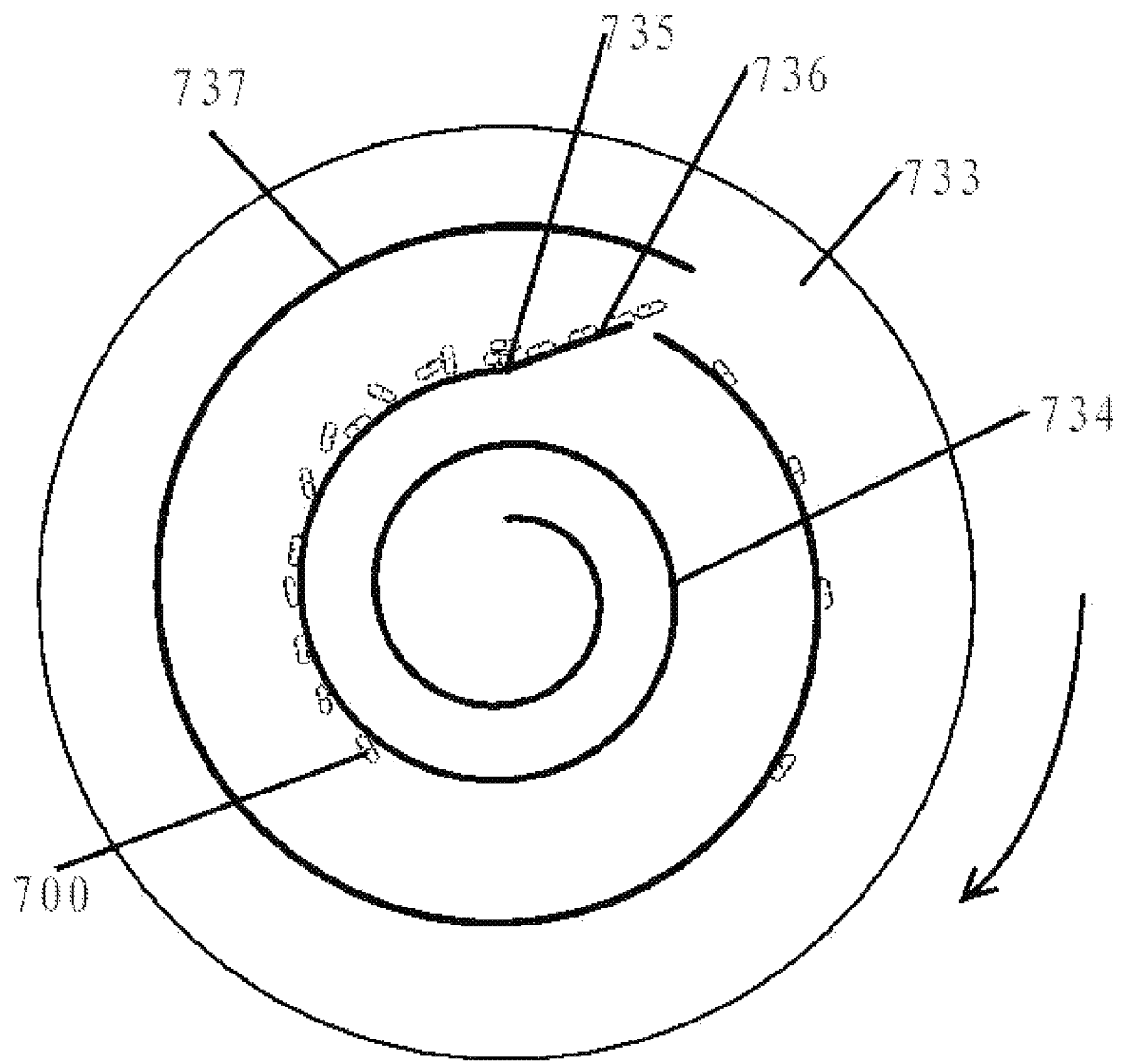
FIG. 15 is a structural diagram of the vortex medication flow passages and mechanical stiffing plate of preferred embodiment 7.

As shown in FIG. 14 and FIG. 15, the difference between the preferred embodiment 7 and the preferred embodiment 4 is that the separation body is a vortex passage. The vortex passage comprises at least one stiffing plate, an inner vortex, a rotary shaft and an outer vortex. As shown in FIG. 14, the medications 700 move along the inner vortex 734 driven by the rotary disc 733, when the stiffing plate 736 is turned toward the inner side of the rotating shaft 735, as long as the friction force between the medications 700 and the rotary disc 733 is larger than the centrifugal force of the medications 700, the medications 700 still rotate along with the rotary disc 733 at the same radius when the medication 700 leaves the stirring plate 736. As shown in FIG. 15, if the stirring plate 736 is turned toward the outer side of the rotating shaft 735, the medications 700 enter the outer vortex 737 along the stiffing plate 736. By actively control the turning frequency of the stiffing plate 736 toward outer side, the distance between medications can be effectively opened up, thus accurate medication dispensing can be realized. Similarly, multi-stage stiffing plates can be adopted to achieve better medication separation. All other principles are the same as that of the preferred embodiment 4, and are not repeated herein.

Preferred Embodiment 8

Figure 16:
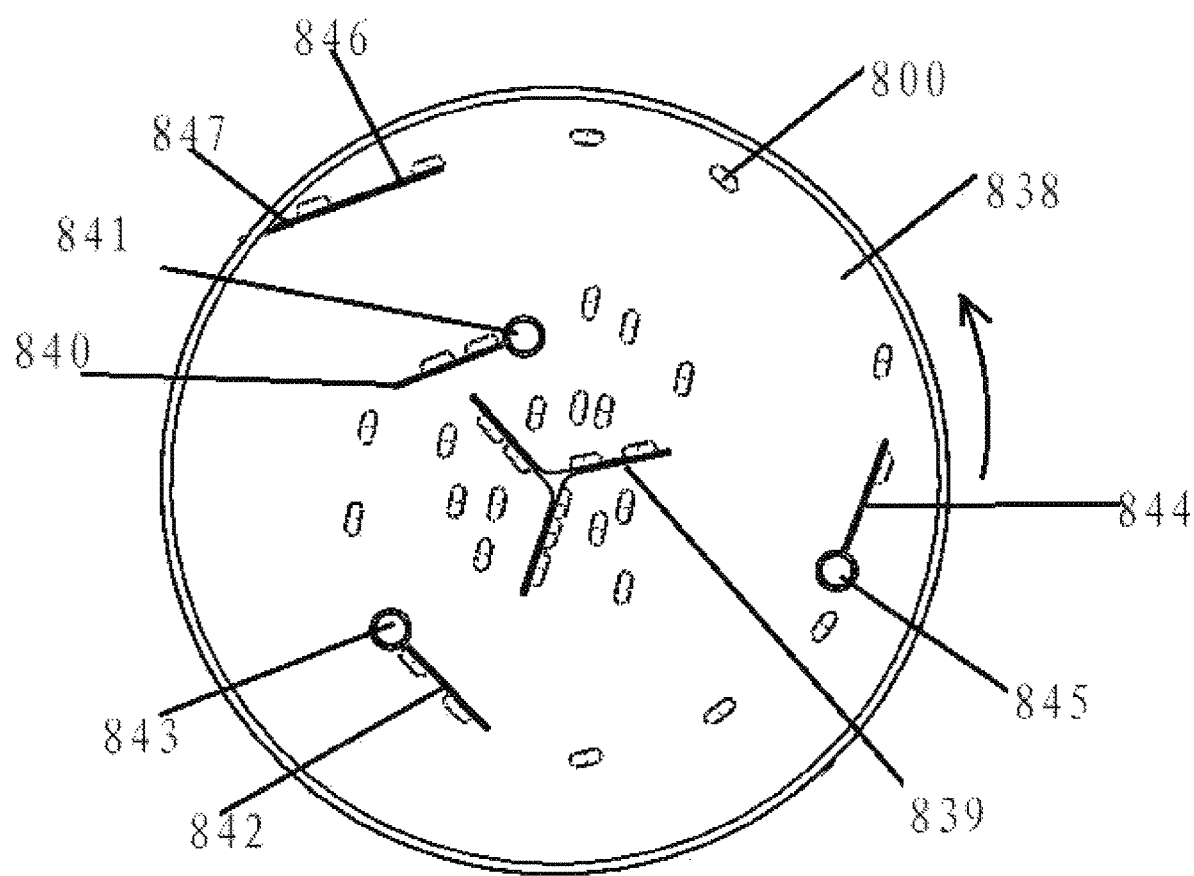
FIG. 16 is a structural diagram of the rotary disc, active shifting fork and actively controlled stiffing plates of preferred embodiment 8.

As shown in FIG. 16, the difference between the preferred embodiment 8 and the preferred embodiment 4 is that the separation body is an active shifting fork, a rotary disc, active stiffing plates and their coordination with each other. As shown in FIG. 16, in a preferred embodiment, the medications 800 fall near the center of the rotary disc 838. Driven by the active shifting fork 839 and moved by rotary disc 838, the medications 800 firstly enter the radius range of the first active stiffing plate 840. If the first active stirring plate 840 turns toward the inner side around the first rotary shaft 841, as long as the friction force between the medications 800 and the rotary disc 838 is larger than the centrifugal force of the medications 800, the medications 800 continue to rotate with the rotary disc 838 at the current radius. If the first active stiffing plate 840 is turned toward the outer side around the first rotary shaft 841, the medications 800 enter the radius range of the second active stiffing plate 842 along the first stiffing plate 840. If the second active stiffing plate 842 turns toward the inner side around the second rotary shaft 843, the medications 800 continue to rotate with the rotary disc 838 at the current radius. If the second active stiffing plate 842 turns toward the outer side around the second rotary shaft 843, the medications 800 enter the radius range of the third active stiffing plate 844 along the second stiffing plate 842. If the third active stiffing plate 844 turns toward the inner side around the third rotary shaft 845, the medications 800 continue to rotate with the rotary disc 838 at the current radius. If the third active stiffing plate 844 turns toward the outer side around the third rotary shaft 845, the medications 800 enter the radius range of the outlet along the third active stiffing plate 844, the medications 800 reaches the outlet 847 through a baffle plate 846. The distance between the first rotary shaft 841, the second rotary shaft 843, the third rotating shaft 845 and the center of the rotary disc 838 is increased in sequence, but the distance between the first active rotary shaft 841 and the center of the rotary disc 838 is larger than the outer contour of the active shifting fork 839. By actively control the turning frequency toward outer side of the first active stiffing plate 840, the second active stiffing plate 842 and the third active stiffing plate 844, the distance between medications can be effectively opened up, thus accurate medication dispensing can be realized. Obviously, the number of active stiffing plates can be one or a plurality of them. All other principles are the same as that of the preferred embodiment 4, and are not repeated herein.

According to the above embodiments, the present invention further provides methods of solid medication automatic separation, wherein the advancing speed of the medications entering the said medication separation device is gradually increased along the medication flow passage in a slow-feeding and fast-discharging mode, the increase of medication advancing speed can be non-continuous and reaches maximum at the outlet of the said medication separation device so that effective separation between the medications is realized. Movements of medications are realized through part or all of the five factors comprising friction force, centrifugal force, gravity, mechanical stiffing and limit the moving directions in the medication passage. The methods of solid medication automatic separation are also suitable for separating solid substances.

Different from the existing technologies, the advantages of the present invention a full automatic medication dispensing system and methods of solid medication separation are as follows:

(1) When medications are processes based on the automatic dispensing principle, structure and methods through slow feeding and fast discharging in medication flow passages, the system has no requirement on the size, shape and weight of any solid medications, namely, as long as the medications are solid, the system can automatically dispense and supply the medications.

(2) The system only requires one time input of a series sets of medication taking time, medication type and quantity to dispense the medications automatically, accurately and efficiently into a sealed medication supply box according to the set parameters, and the excessive medications are automatically returned to the medication retrieving bottles. The system is convenient and safe to use with high accuracy.

(3) When it is time to take medications, the system can remind the medication taking person in time and automatically supply the medications after confirmation. The system can inform preset personnel when a dose of medications are not taken after a preset period of time.

(4) The problem of medication storage in a sealed container is solved because the medication supply box is sealed and the original medication bottles are also sealed after their original covers are put back on.

(5) All parts in contact with medications can be conveniently detached and cleaned or opened and cleaned, and can be conveniently mounted together and can not be assembled in a staggered manner, so that a clean medication dispensing and storage environment is realized.

(6) The fixed medication supply box and the portable medication box meet the requirements of different medication taking people, and the portable medication box can be manually filled with medications and used independently.

(7) The status of the system just before power outage can be automatically resumed to continue to run after the power supply is restored.

(8) The system eliminated the possibility of medication dispensing errors, avoided the possible contamination caused by manual medication dispensing, made the medication dispensing and medication taking process very convenient, greatly increased the proportion of people taking medications on time and accurately, and thus is of great medical, economical and practical value.

The above are only preferred embodiments of the present invention, not intend to restrict the protective scope of the invention. Any equivalent structural or procedural change made from or out of the description of this invention or direct or indirect use thereof in any related technical field fall within the protective scope of this patent.

The invention claimed is:

1. A medication dispensing system, comprising:
a hopper, the hopper having at least one outlet;
a separator, the separator comprising:
a first rotating disc with an inlet in communication with the at least one outlet of the hopper to receive material from the hopper;
a second rotating disc concentric with the first rotating disc, the second rotating disc having a sidewall extending about an outer periphery and an outlet at the outer periphery of the second rotating disc; and
a vortex passage formed by a wall having a first end and a second end, the second end of the wall spaced radially outwardly of the first end of the wall and radially inwardly of the sidewall;
a distribution channel extending between the outlet of the separator and an inlet of a supply box or a retrieving bottle; and
a central processing unit,
wherein the first rotating disc moves at a first speed and the second rotating disc moves at a second speed, the second speed being greater than the first speed,
wherein the first rotating disc has an outer circumference equal to an inner circumference of the second rotating disc,
wherein the first rotating disc and the second rotating disc are coplanar at a joint of the outer circumference of the first rotating disc and the inner circumference of the second rotating disc, and
wherein the wall forming the vortex passage is greater than one revolution to overlap itself in the radial direction and extends across the joint between the outer circumference of the first rotating disc and the inner circumference of the second rotating disc.

2. The medication dispensing system of claim 1, wherein the hopper has dividing walls forming a plurality of cells, wherein each cell holds one type of medication and has an outlet at the bottom, and the outlet of the cell is matched with the inlet of the separator, and
wherein an amount of medications entering the separator is controlled by changing the relative positions of the outlet of a cell and the inlet of the separator.

3. The medication dispensing system of claim 1, further comprising a fixed disc under the separator, the fixed disc having an inlet,
wherein the fixed disc has a retainer for at least one bottle and at least one bottle retained in the retainer, the retainer being on a periphery of the fixed disc.

4. The medication dispensing system of claim 3, wherein the distribution channel has a first pathway extending to the inlet of the fixed disc and a second pathway extending to the at least one bottle.

5. The medication dispensing system of claim 4, wherein the distribution channel has a sensor to count a number of items passing through the distribution channel, and
wherein the first pathway or second pathway is chosen based on the number of items passing through the distribution channel.

6. The medication dispensing system of claim 1, wherein the separator has a plurality of concentric rotating discs with a radially outward one of the plurality of concentric rotating discs rotating at a higher speed than an radially inward one of the plurality of concentric rotating discs.

7. The medication dispensing system of claim 1, wherein the first rotating disc has an upwardly extending projection in a center of the first rotating disc.

8. The medication dispensing system of claim 1, further comprising a stirring plate attached to an end of the vortex passage.

9. The medication dispensing system of claim 1, further comprising a polygon shape or a multiple-arc shape medication flow passage.

10. The medication dispensing system of claim 1, further comprising a shifting fork mounted at a center of the first rotating disc and at least one shifting plate located radially outwardly of the center of the first rotating disc.

11. The medication dispensing system of claim 3, further comprising a supply box under the fixed disc,
wherein the supply box has a plurality of cells.

12. The medication dispensing system of claim 11, further comprising:
a first outlet and a second outlet formed in a bottom of the supply box, the first outlet located radially outward of the second outlet; and
a shifting cover mounted to the bottom of the supply box, wherein the shifting cover can selectively cover only the second outlet or both the first outlet and the second outlet.

13. The medication dispensing system of claim 11, wherein the supply box is a portable medication box, the portable medication box comprising:
a sidewall and a cover, an opening formed in the cover; and
a medication channel extending upward from the opening toward the fixed disc.

14. The medication dispensing system of claim 1, wherein the first rotating disc includes a center of the separator.

15. A medication dispensing system, comprising:
a hopper, the hopper having at least one outlet;
a separator, the separator comprising:
a first section extending from a center of the separator and having an inlet in communication with the at least one outlet of the hopper to receive material from the hopper and an outlet; and
a second section having an inlet receiving the material from the first section and an outlet, the first section and second section being vertically spaced from one another, the inlet of the second section being below an entirety of the first section;
a distribution channel extending between the outlet of the separator and an inlet of a supply box or a retrieving bottle; and
a central processing unit,
wherein the first section moves at a first speed and the second section moves at a second speed, the second speed being greater than the first speed,
wherein the first section and the second section are concentric, and
wherein a diameter of the first section is less than a diameter of the second section.

16. The medication dispensing system of claim 15, wherein the first section has a sidewall, and
wherein the outlet of the first section is in the sidewall of the first section.

17. A medication dispensing system, comprising:
a hopper, the hopper having at least one outlet;
a separator, the separator having an inlet in communication with the at least one outlet of the hopper and an outlet at a periphery of the separator;
a shifting plate pivotable about a first end between a first position and a second position to selectively move medication radially outwardly;
a distribution channel extending between the outlet of the separator and an inlet of a supply box or a retrieving bottle;
a central processing unit; and
a first vortex divider having a first end and a second end spaced radially outwardly from the first end to form a first path and a second vortex divider having a first end spaced radially inwardly from an edge of the separator and a second end spaced radially outwardly from the first end to form a second path,
wherein the first end of the shifting plate is located at the second end of the first vortex divider to selectively move medication from the first path to the second path.

18. A medication dispensing system, comprising:
a hopper, the hopper having at least one outlet;
a separator, the separator having an inlet in communication with the at least one outlet of the hopper and an outlet at a periphery of the separator;
a shifting plate pivotable about one end between a first position and a second position to selectively move medication radially outwardly;
a distribution channel extending between the outlet of the separator and an inlet of a supply box or a retrieving bottle;
a central processing unit;
an active shifting fork extending radially outwardly from a center of the separator; and
a plurality of shifting plates spaced radially outwardly from the active shifting fork and inwardly from the periphery of the separator and spaced from one another in a circumferential direction, each shifting plate rotatable about a shaft, the shaft being spaced inwardly of the periphery of the separator.

* * * * *